United States Patent [19]

Neckers

[11] Patent Number: 4,752,649

[45] Date of Patent: Jun. 21, 1988

[54] PERESTER PHOTOINITIATORS

[75] Inventor: Douglas Neckers, Perrysburg, Ohio

[73] Assignee: Bowling Green State University, Bowling Green, Ohio

[21] Appl. No.: 644,541

[22] Filed: Aug. 27, 1984

Related U.S. Application Data

[63] Continuation-in-part of Ser. No. 584,645, Feb. 29, 1984, abandoned.

[51] Int. Cl.[4] .................................. C07C 179/18
[52] U.S. Cl. .................................. 560/302
[58] Field of Search ............... 260/502 R, 453 RZ; 560/302

[56] References Cited

U.S. PATENT DOCUMENTS

| | | | |
|---|---|---|---|
| 2,456,408 | 12/1948 | Greenlee | 260/410.5 |
| 2,484,487 | 10/1949 | Caldwell | 560/209 |
| 2,575,440 | 11/1951 | Bradley | 526/313 |
| 4,129,586 | 12/1978 | Sheppard | 260/465 D |
| 4,416,826 | 11/1983 | Neckers | 260/453 RZ |

OTHER PUBLICATIONS

Abu-Abdoun et al., *Chemical Abstracts*, vol. 100, No. 68776w, 1984.
Leffler et al., 93 *Journal of American Chemical Society*, 7005 (1981).
Walling et al., 87 *Journal of American Chemical Society*, 3413 (1965).
Thijs et al., *Journal of Organic Chemistry*, vol. 44, No. 23, pp. 4123–4128 (1979).
Rossner et al., *Chemical Abstracts*, vol. 89, No. 41579b, (1978).
Swern, Organic Peroxides, vol. 1, Wiley-Intersciences, New York, pp. 285–289 310 (1979).
Bartlett et al. 1, *J. Am. Chem. Soc.*, vol. 82, pp. 1753–1756 (1960).
Bartlett et al. 11, *J. Am. Chem. Soc.*, vol. 82, pp. 1756–1762 (1960).
Ruchardt, *Agnew, Chem. Internat. Edit.*, vol. 9, p. 830 (1970).

*Primary Examiner*—Donald B. Moyer
*Assistant Examiner*—Bruce D. Gray
*Attorney, Agent, or Firm*—Emch, Schaffer, Schaub & Porcello Co.

[57] ABSTRACT

Peresters of the formula: ROOC—$R_1$—COOOR wherein R is an alkyl group; $R_1$ is selected from the group including ketone (unsubstituted or substituted) groups, and $R_1$ is any group absorbing radiation between 250 and 800 nm such that $R_1$ produces an excited state of sufficient lifetime to cause the decomposition to free radicals of the appended perester or peroxidic function.

2 Claims, 22 Drawing Sheets

PERESTER PHOTOINITIATORS

BACKGROUND OF THE INVENTION

1. Technical Field

The present invention is based upon work supported by the National Science Foundation under NSF Grant DMR 81-03100.

The present patent application is a continuation-in-part of the Neckers patent application, Ser. No. 584,645, filed Feb. 29, 1984 abandoned.

The present invention is concerned with new organic compounds which are particularly suitable as photoinitiators. The present invention is especially concerned with peresters. The peresters of the present invention are especially useful as photoinitiators for the polymerization of ethylenically unsaturated materials.

2. Background Art

Photoinitiators are free-radical sources which decompose photochemically and are employed especially as initiators in the polymerization of ethylenically unsaturated materials. In view of the efficient control photoinitiated polymerization offers, such has assumed great importance in recent years in the printing and electronics industries such as in printing inks, paints and photoresist coatings.

Among typical commercial initiators are three general types: mixtures of aryl ketones, benzoin ethers, or substituted acetophenones. In past years, highly halogenated aryl hydrocarbons were also used for initiators, but their use is now precluded because they are so highly toxic.

Among the more important commercially used photoinitiators for acrylate polymerization is the so-called "Hammond initiator", benzophenone-Michler's ketone.

A major advantage of the Hammond initiator is the rate by which it initiates radical chain reactions; two important disadvantages are the rather large amount of initiator needed to make the rate of polymerization sufficiently rapid for printing applications and the potential toxicity of one of the initiator partners—Michler's ketone(4,4'-bis(N,N-dimethylamino)benzophenone).

To be of real practical significance as a photoinitiator, a compound must be relatively thermally stable but must also be labile when irradiated with wavelengths of UV or visible light. Accordingly, providing new compounds which possess this combination of properties is quite difficult. For instance, various benzophenone derivatives of benzoyl peroxide have been studied. For example, see Leffler et al; Journal American Chemical Society; 1971, 93, 7005 et seq. However, such derivatives are not especially stable thermally. It has also been noted that the photochemical efficiency of triplet benzophenone sensitized decompositions of peroxides in solution is low (e.g. see Walling et al., Journal American Chemical Society, 1965, 87, 3413 et seq.).

SUMMARY OF THE INVENTION

An object of the present invention is to provide new compounds which have the requisite combination of relative thermal stability and efficient photodecomposability to be effective and practical photoinitiators.

The compounds of the present invention are peresters which contain a light absorbing chromophoric moiety. The compounds of the present invention exhibit thermal stability characteristics. However, the compounds of the present invention, unlike prior known peresters, are readily photodecomposable and effective photoinitiators for the polymerization of ethylenically unsaturated compounds. The present invention also makes it possible to control or tune the photodecomposition of the compounds by the absorption characteristics of the light-absorbing chromophore portion of the compound.

The compounds of the present invention are represented by the general formula:

Chromophore—COOOR or

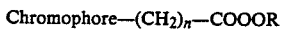
Chromophore—(CH$_2$)$_n$—COOOR where chromophore is selected from the group including aryl groups, arylalkyl groups, or heteroaryl groups, absorbing radiation between 250–800 nm, and R is an alkyl group or arylalkyl group.

The compounds of the present invention are represented by the formula:

R$_1$Y—Ar COOR where Ar is selected from the group including phenyl (unsubstituted or substituted) groups; naphthyl groups; anthryl groups, pyryl groups, phenanthryl groups, heteroaromatic groups, and heterocyclic groups, including furan, thiophene, benzothiophene, benzothiazole, etc; Y is selected from the groups including CH$_2$, C=O, C=N; R is an alkyl group, and R$_1$ is any group absorbing radiation between 250 and 800 nm and R is an organic group such that the group R$_1$ produces an excited state of sufficient lifetime to cause the decomposition to free radicals of the appended perester or peroxidic function.

The present invention is concerned with the photoinitiated polymerization of vinylmonomers by benzophenone t-butyl peresters.

The present invention is also concerned with photopolymerizable compositions comprising at least one photopolymerizable ethylenically unsaturated material and at least one of the above-discussed peresters.

Moreover, the present invention is concerned with polymerizing the above-defined photopolymerizable compositions by subjecting such to light, and polymer obtained thereby.

DESCRIPTION OF BEST AND VARIOUS MODES

Figure 1:
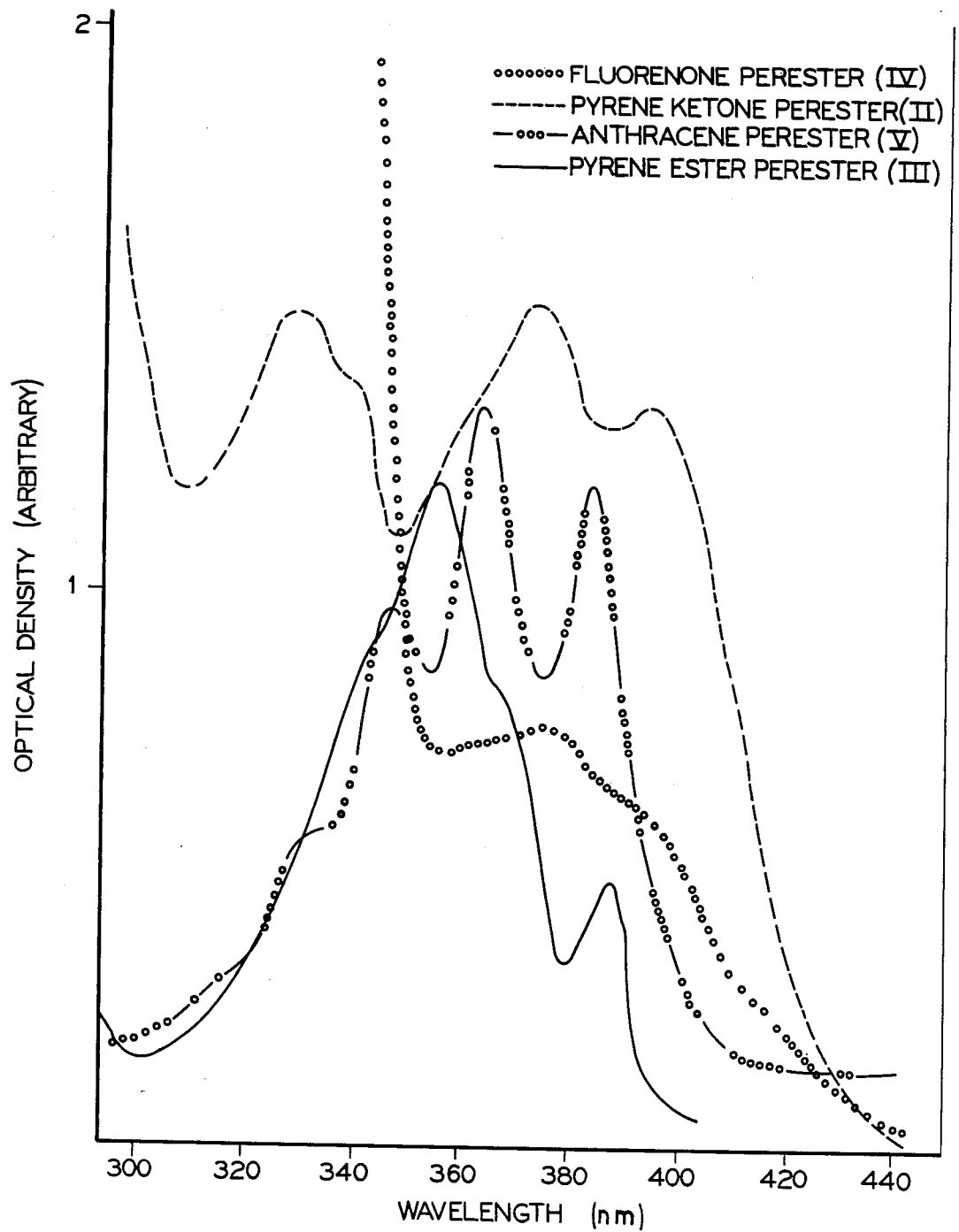
FIG. 1 is a graph showing UV spectra in dichloromethane.

The compounds of the present invention are represented by the formula:

where Ar is selected from the group including phenyl (unsubstituted or substituted) groups; naphthyl groups; anthryl groups, pyryl groups, phenanthryl groups, heteroaromatic groups or heterocyclic groups, including furan, thiophene, benzothiophene, benzothiazole, etc; Y is selected from the group including $CH_2$, $C=O$, $C=N$ etc., R is an alkyl group, and $R_1$ is any group absorbing radiation between 250 and 800 nm and $R_1$ is an organic group such that the group $R_1$ produces an excited state of sufficient lifetime to cause the decomposition to free radicals of the appended perester or peroxidic function.

Examples of some suitable $R_1$ groups are aryl groups, heteroaryl groups, polycyclic aryl groups, aralkyl groups, and substituted examples of all of these. Examples also include those containing heteroatoms such as oxygen, sulfur, nitrogen, phosphorus, etc.

Examples of other suitable $R_1$ groups are alkyl groups, cycloalkyl groups, and groups containing heteroatoms, such as oxygen, sulpher, nitrogen, etc. Generally the $R_1$ groups contain from 1 to 22 carbon atoms, preferably 1–12 carbon atoms; and in conjunction with Y—Ar, they must absorb radiation between 250–800 nm. range.

Examples of some alkyl groups are methyl, ethyl, t-butyl, t-amyl, hexyl, 2-ethylhexyl, nonyl and octodecyl.

Examples of some suitable aryl groups include phenyl, phenanthryl, and anthracyl.

Examples of some cycloalkyl radicals include cyclopropyl, cyclopentyl, cyclobutyl, cyclohexyl, cycloheptyl, cyclooctyl, and cyclododecyl.

Examples of some aralkyl groups are phenylmethyl and naphthylethyl.

Examples of some alkaryl groups include tolyl, xylyl and cumyl.

Examples of substituted aryl groups in addition to alkaryl include alkoxy-substituted aryl groups, such as methoxyphenol. The substituted aryl groups usually contain 1, 2 or 3 substitutions which are usually ortho and/or para with respect to the carbonyl group to which the substituted aryl group is connected.

The heterocyclic groups generally contain 5–6 members in the range and contain S, O and/or N in the ring and include morpholinyl, piperidyl, thiophenyl, and furanyl.

The preferred $R_1$ groups are aryl and substituted aryl groups and the most preferred $R_1$ groups are phenyl and alkyl and/or alkoxy-substituted phenyl wherein the alkyl and/or alkoxy groups contain 1 to 2 carbon atoms and preferably 1–12 carbon atoms.

The two carbonyl groups located on the benzene rings can be ortho, meta, or, preferably, para to each other.

The synthesis was based on a general perester of the formula:

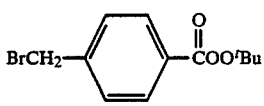

Formula I

The initiators of interest are, with the exception of Formula II, non-conjugated peresters based on pyrene, anthracene, and fluorenone as indicated below.

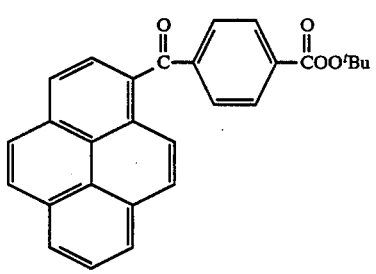

Formula II

Formula III

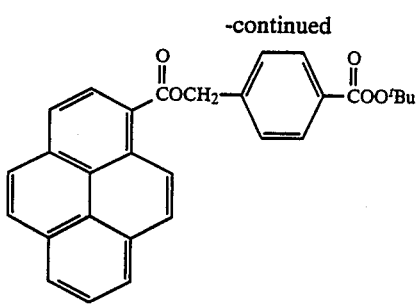

Formula IV

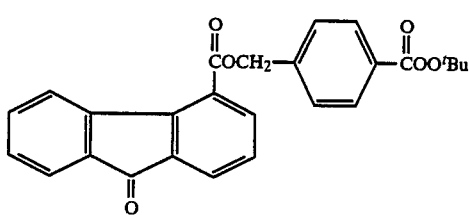

Formula V

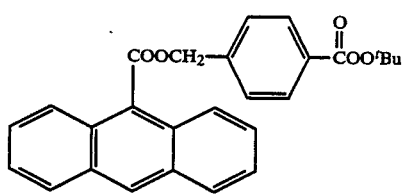

The compounds of the present invention can be readily obtained from the corresponding carboxylic acids. In particular, the corresponding carboxylic acid can be reacted at elevated temperature (e.g. up to about 60° C.), preferably at reflux, with, for example, thionyl chloride to form the corrresponding acid chloride. Next, the acid chloride can be reacted with a hydroperoxide, such as tert-butyl hydroperoxide in the case of R being t-butyl, usually in the presence of a tertiary amine, preferably triethylamine. In addition, it is preferred that this stage of the preparation be carried out in the presence of a diluent, such as ether, benzene, or dichloromethane.

The compounds of the present invention are especially useful as photoinitiators in the polymerization of photopolymerizable ethylenically unsaturated materials. The photopolymerizable materials can be monomeric or prepolymers containing one or more ethylenically unsaturated groups.

Examples of some suitable photopolymerizable materials include esters of unsaturated monocarboxylic acids or dicarboxylic acids, e.g. esters of acrylic acid, methacrylic acid, α-cyanacrylic acid, sorbic acid, fumaric acid or itaconic acid with aliphatic, cycloaliphatic or aromatic, aliphatic monohydric to tetrahydric alcohols of 3 to 20 carbon atoms, e.g. methyl acrylate and methacrylate; n-, i- and t-butyl acrylate and methacrylate; 2-ethylhexyl acrylate; lauryl acrylate; dihydrodicyclopentadienyl acrylate and methacrylate; methylglycol acrylate; hydroxyethyl acrylate and methacrylate; hydroxypropyl acrylate and methacrylate; ethylene glycol diacrylate; diethylene glycol diacrylate; triethylene glycol diacrylate; neopentylglycol diacrylate and dimethacrylate; 1,4-dimethylolcyclohexane diacrylate; pentaerythritol-triacrylate,-tetraacrylate,-trimethacrylate and -tetramethacrylate; ethyl α-cyanoacrylate; ethyl crotonate, ethyl sorbate; diethyl fumarate; and the diacrylate and dimethacrylate or oxyalkylated bisphenol A; amides of acrylic acid or methacrylic acid which may or may not be substituted at the nitrogen by alkyl, alkoxyalkyl or hydroxyalkyl, e.g., $N_1N'$-di-methylacrylamide, N-isobutylacrylamide, diacetoneacrylamide; N-methylolacrylamide, N-methoxymethylacrylamide, N-butoxymethylolarylamide, N-butoxymethylmethacrylamide and ethylene glycol bis(N-methylolacrylamide)ether; vinyl esters of monocarboxylic acids or dicarboxylic acids of 2 to 20 carbon atoms; e.g., vinyl acetate; vinyl propionate, vinyl 2-ethylhexanoate, vinyl versatate and divinyl adipate; vinyl ethers of monohydric or dihydric alcohols of 3 to 20 carbon atoms, e.g., isobutyl vinyl ether, hexyl vinyl ether, octadecyl vinyl ether, ethylene glycol divinyl ether, diethylene glycol divinyl ether, butanediol divinyl ether and hexanediol divinyl ether; mono-N-vinyl compounds, e.g., N-vinylpyrrolidone, N-vinylpiperidone, N-vinylcaprolactam, N-vinylmorpholine, N-vinyloxazolidone, N-vinylsuccinimide, N-methyl-N-vinylformamide and N-vinylcarbazole; allyl ethers and allyl esters, e.g., trimethylolopropane diallyl ether, trimethylolpropane triallyl ether, pentaerythritol triallyl ether, diallyl maleate, diallyl fumarate or diallyl phthalate; vinyl and vinylidine halides, e.g., vinyl chloride and vinylidene chloride; and vinyl aromatics, e.g., styrene, alkyl styrenes, halostyrenes and divinylbenzenes.

Examples of some polymeric photopolymerizable materials include unsaturated polyester obtained, for instance, from α,β-unsaturated dicarboxylic acids, e.g., maleic acid, fumaric acid or itaconic acid, and aliphatic, cycloaliphatic or non-phenolic aromatic diols, e.g., ethylene glycol, diethylene glycol, triethylene glycol, propane-1,2-diol, propane-1,3-diol, butane-1,2-diol, butane-1,3-diol, butane-1,4-diol, but-2-ene, 1,4-diol, neopentylglycol, hexane-1,6-diol or oxyalkylated bisphenol A; unsaturated epoxide-acrylates obtained, for instance, from monofunctional epoxides and acrylic acid or methacrylic acid, by the method of U.S. Pat. No. 2,484,487, bifunctional epoxides and unsaturated fatty acids, by the method of U.S. Pat. No. 2,456,408 polyfunctional aromatic epoxides and crotonic acid, by the method of U.S. Pat. No. 2,575,440 or polyfunctional aromatic or aliphatic fatty glycidyl ethers and acrylic acid or methacrylic acid, by the method of U.S. Pat. No. 2,842,851; unsaturated polyurethanes (urethaneacrylates) prepared from hydroxyalkyl acrylates and diisocyanates, with or without polyols or polyamines; unsaturated copolymers, prepared, for example, by reacting copolymers, containing maleic anhydride groups, with unsaturated alcohols; or acrylic ester copolymers containing carboxylic acid groups or polyesters containing carboxylic acid groups with unsaturated epoxides, e.g., glycidyl acrylates; butadiene polymers in which the double bonds are predominantly present as vinyl side chains; diallyl phthalate prepolymers; and poly-N-vinylurethanes, e.g. prepared, for instance, by reacting vinyl isocyanate with saturated or unsaturated polyesterpolyols, polyether-polyols or polyfunctional alcohols.

The peresters when employed as photoinitiators are usually present in amounts of about 1 to about 10%, and more usually about 1 to about 3% by weight based upon the weight of the photopolymerizable material present. The polymerization of such compositions can be carried out by subjecting or exposing the compositions on light (e.g., UV or visible) of appropriate wavelength absorbable by the chromophore moiety of the perester employed. The compounds of the present invention can be tailored by the particular chromophore group present to provide light absorption properties for a given wavelength selected from a broad spectrum of wavelengths, preferably in the visible and UV ranges. It is preferred that the chromophore group be selected so that it absorbs light in the range of about 250–800 nm. The particular wavelength to employ is determinable by those skilled in the art without undue experimentation once they are aware of the present invention and the particular chromophore group present.

Polymers obtained from polymerization in the presence of the peresters of the present invention have been found to contain as end group the chromophore group from the perester employed; and, therefore, can subsequently be subjected to irradiation to achieve some crosslinking.

Polymerization of the composition usually requires exposure to the light for about 30 seconds to about 10 minutes depending upon the amount of initiator present. The time and amount are inversely related. The crosslinking reaction is usually about $10^2$ to $10^3$ times slower than the polymerization and usually requires about 1 to about 20 hours depending upon the amount of initiator employed.

The following non-limiting examples are presented to further illustrate the present invention:

EXAMPLE 1

Preparation of Peresters

Starting materials and other reagents were obtained from Aldrich Chemical Company and purified, where necessary, by standard procedures. The monomers, MMA and styrene, were freed of inhibitor by washing with a 5% NaOH solution followed by repeated washing with distilled water. The monomers were then dried and distilled under reduced pressure just prior to use. All melting points are uncorrected. Ultraviolet spectra were obtained on a Varian Model 219 spectrometer. The intensity of the radiation was monitored constantly by benzophenone/benzhydrol actinometry at 30° and observed to be $9.15 \times 10^{17}$ quanta/minute, as described by L. Thijs, S. N. Gupta and D. C. Neckers, *J. Org. Chem.* 44, 4123 (1979).

4-Bromomethyl Benzoyl Chloride and -peroxybenzoic acid, tert-Butyl Ester (Crucial Perester Intermediate Formula I)

4-Bromomethyl benzoic acid (18.53 g., 0.086 moles) which had been prepared by the Tuleen method, D. L. Tuleen and B. A. Hes, *J. Chem Ed.* 40, 476 (1971), and finely powdered was refluxed for one hour with an excess of thionyl chloride and a few drops of pyridine. A rapid evolution of hydrogen chloride took place for a few minutes and then stopped. Excess thionyl chloride was distilled off under vacuum and the oily residue dissolved in hexane. Crystallization occurred soon in the refrigerator. Filtration gave 14.32 g (71% yield) of the acid chloride.

Preparation of Formula I Perester

To an ice-salt cooled solution of 13.22 g (56 mmols) of 4-bromoethyl benzoyl chloride in 125 ml of dry ether was added dropwise over 30 minutes under magnetic stirring a solution of 5.45 g (60 mmole) of tert-butyl hydroperoxide and 6.56 g (65 mmoles) of triethylamine in 50 ml of ether. After the addition of mixture was stirred for another hour. Filtration and evaporation left a solid. This was dissolved in dichloromethane and chromatographed over silica gel with dichloromethane as eluent. This gave 16.46 g of a colorless perester (90% yield) which was further purified by vacuum sublimation. The pure sample melted at 93°–4°.

IR(KBr) 1760 cm$^{-1}$ (C=O perester).

NMR (CDCL$_3$) $\delta = 1.44$ s 9H CH$_3$; 4.52, s 2H, CH$_2$; 7.44–8.00, 9H aromatics.

Synthesis of 4-[(1-Pyrenyl)carbonyl]-Peroxybenzoic Acid, tert-Butyl Ester Formula II Pyrene, (6.75 g; 0.033 mol) was dissolved in 75 ml of dry benzene. 4-Carbomethoxybenzoyl chloride (6.0 g; 0.030 mol) was added. To this solution 6.75 g (0.050 mol) of aluminum chloride was gradually added. A dark color developed. After the addition of AlCl$_3$ the temperature increased slightly and then the temperature of the mixture was increased to 40° with a water bath and gradually recooled to room temperature. The reaction mixture was then poured into an ice bath to which 5 ml of HCl has been added. The benzene was removed by steam distillation. The organic mixture was extracted with benzene and dried over magnesium sulfate. The solvent was evaporated and the residue chromatographed on silical gel with hexane. Elution with carbon tetrachloride gave pyrene, 3.2 g. Elution with carbon tetrachloride/chloroform (1:2) gave a yellow solid in two fractions (1.62 g; 3.25 g). The former fraction contained some pyrene. The latter fraction was extracted with hot ethanol to give 2.55 g of a yellow solid (mp. 141°–144°), identified as 4-[(1-pyrenyl)carbonyl]methyl ester. From the 1.62 g in fraction one of the eluted ketone, 1.01 g was obtained.

4-[(1-Pyrenyl)carbonyl]benzoic acid, methyl ester (2.55 g; 7 mmol) was dissolved in 25 ml of benzene. A solution of 354 mg (6.4 mmol) of KOH in 5 ml MeOH was added, and the mixture boiled. Precipitation of the potassium salt occurred. The mixture was extracted with water to give a yellow water layer which was acidified with dilute HCl to give a light yellow precipitate. Filtration gave 1.73 g (5 mmol) of the 4-[(pyrenyl)carbonyl]benzoic acid.

IR 3600–3350 cm$^{-1}$; 1710 cm$^{-1}$; 1665 cm$^{-1}$.

4-[(1-Pyrenyl)carbonyl]benzoic acid (1.73 g; 5 mmol) was refluxed with 10 ml of SOCl$_2$ and 3 drops of pyridine for 3 hours. A yellow/brown solution resulted. The excess thionyl chloride was evaporated and the residue triturated with ether/hexane and filtered to give the yellow acid chloride.

IR: 1652 cm$^{-1}$; 1770 cm$^{-1}$.

The acid chloride was dissolved in 60 ml of a benzene/chloroform mixture (50/10) and a mixture of tert-butyl hydroperoxide (5.2 mmol) and triethylamine (606 mg; 6 mmol) was added. After the addition the mixture was stirred for 2 hours at room temperature and then heated to 50° for a few minutes.

The solvent was evaporated and the residue dissolved in dichloromethane and chromatographed over silica gel. Elution with CH$_2$Cl$_2$ gave a yellow band which oiled when the solvent contained no perester. Elution was continued in the dark to give 1.50 g of a dark yellow oil which, when heated with cyclohexane/benzene dissolved. After several days in the refrigerator light yellow crystals formed which analyzed as the Formula II perester.

IR 1660 cm$^{-1}$ ($\nu$C=O ketone); 1770 cm$^{-1}$ ($\nu$C=O adjacent to perester).

NMR (CDCl$_3$) $\delta=1.43$, s, 9H; CH$_3$; $\delta=7.9$–8.4 m, 13H; aromatic protons.

Analysis: Calc. for C$_{28}$H$_{22}$O$_4$: C=79.55; H=5.25. Found: C=79.40; H=5.32.

4-[(1-Pyrenyl)carbonyloxymethyl]Peroxybenzoic Acid, tert-Butyl Ester (Formula III)

Pyrene-1-carboxylic acid (1 g, 4 mmoles) was converted into the dry potassium salt as previously described. A suspension of the potassium salt, 0.65 g of the bromomethyl Formula I perester (2 mmoles) and 60 mg of 18 crown-6-(0.23 mmoles) was stirred for 60 hours in the dark. Evaporation and chromatography of the residue over silica gel with carbon tetrachloride/chloroform 1:1 as eluent gave 1.0 of yellow oil. Recrystallization from cyclohexane gave 0.82 g of crystals, m.p.=105°-08°. Another recrystallization raised the melting point 2°.

IR (KBr) 1750 cm$^{-1}$ ($\nu$C=O adjacent to perester), 1720 cm$^{-1}$ ($\nu$C=O ester).

NMR (CDCl$_3$) $\delta=1.41$, s, 9H, CH$_3$; $\delta=5.56$, s, 2H, CH$_2$; $\delta=7.55$–9.32, m, 13H aromatic protons with a doublet for one proton at $\delta=9.26$, a doublet for another proton at $\delta=8.64$ and a doublet for 2 protons at $\delta=7.61$ apparently as part of an AB system.

Analysis: Calc; C=76.99; H=5.32. Found: C=76.81; H=5.39.

Preparation of 4-[(9H-fluorenone-9-one-4-yl)carbonyloxymethyl]-Peroxybenzoic Acid, tert-Butyl Ester (Formula IV)

4-Carboxyfluorenone (896 mg, 4 mmoles) was treated was a suspension in 50 ml of water with an equivalent amount of KOH solution (224 mg KOH; approximately 4 mmoles; pH of the solution close to 7.0). Filtration removed the small amount of undissolved solid and the obtained filtrate was evaporated to dryness. The so obtained potassium salt of the acid was thoroughly dried in an Abderhalen drying apparatus. A suspension was made of the potassium salt in 10 ml of dry acetonitrile and 0.65 of the 4-bromomethyl Formula I perester (2 mmoles) and 60 mg of 18-crown-6(0.23 mmoles) added. The mixture was stirred for 16 hr. in the dark while the progress of the reaction followed by TLC. Evaporation and chromatography, on silica gel with 1:1 carbon tetrachloride/chloroform as the eluting solvent gave 0.85 g of the perester as a yellow oil. Recrystallization from cyclohexane gave yellow crystals, mp. 102°-104°.

IR (KBr): 1750 cm$^{-1}$ ($\nu$C=O adjacent to perester); 1725 cm$^{-1}$ ($\nu$C=O ester); 1710 cm$^{-1}$ ($\nu$C=O ketone).

Analysis: Calc; C=72.56, H=5.11. Found: C=72.65; H=5.15.

NMR (CDCl$_3$) $\delta=1.4$, s 9H, methyl; $\delta=5.4$, s, 2H, methylene; $\delta=7.49$–8.03, m, 11H aromatic protons, 4-[(9-Anthryl)Carbonyloxymethyl]Peroxybenzoic Acid, tert-Butyl Ester (Formula V)

Anthracene-9-carboxylic acid (888 mg., 4 mmol) was converted to the dry potassium salt by the same procedure as above. A suspension of the potassium salt in 10 ml of dry acetonitrile was stirred over the weekend with 0.65 g (2 mmol) of the bromomethyl Formula I perester, and 60 mg (10.23 mmol) of 18-crown-6.

Evaporation and chromatography of the residue as before with carbon tetrachloride/chloroform (1:1) gave a yellow oil (0.82 g.). Recrystallization from cyclohexane gave 0.58 g of yellow crystals; m.p. 118°-119°.

IR (KBr) 1750 cm$^{-1}$ ($\nu$C=O adjacent to perester; 1720 cm$^{-1}$ ($\nu$C=O ester).

NMR: (d-benzene) $\delta=1.70$, s, 9H, CH$_3$; $\delta=5.28$, s, 2H, CH$_2$; $\delta=7.18$–8.09, m, 13H, aromatic protons.

EXAMPLE 2

Decomposition of Peresters By Irradiation and Kinetics Thereof

Photopolymerizations

Photopolymerizations were carried out in sealed, degassed tubes (12 mm diameter) by irradiation at 366 nm with a high pressure mercury arc. After the irradiation period, the polymers obtained were precipitated in methanol and analyzed gravimetrically.

Initiator concentrations for the bulk polymerizations were $2.4 \times 10^{-3}$ mol/l and in the case of solution polymerizations varied as specified in the particular experiment.

Polymer molecular weights were determined in dichloromethane using a Waters Associate Model 440 GPC, and were calculated from elution volumes with reference to polystyrene standards. These standards were used for calibration at a solvent flow rate of 1.5 ml/min. and a polymer concentration of 1 mg/ml, by the method of U.S. Pat. No. 4,416,826.

A series of peresters based on aromatic chromophores which absorb radiation at about 366 nm but which do not produce $\eta$-$\pi$* excited triplet states upon absorption are reported. Three of the peresters were synthesized from crucial intermediate bromomethyl Formula I perester by nucleophilic displacement of bromide ion. One of the Formula II peresters was synthesized directly from the appropriate carboxylic acid by a Friedel Crafts process. A series of routine nucleophilic displacement reactions is carried out on perester containing an appropriate leaving group without disturbing the —O—O— bond of the perester unit. The physical and spectroscopic parameters of the peresters designed are reported in Table 1.

TABLE 1

| Perester Structure | Characteristics of Formula II, III, IV and V Peresters | | |
|---|---|---|---|
| | Extinction Coefficient at 366 nm in CH$_2$Cl$_2$ 1 mol$^{-1}$cm$^{-1}$ | m.p.° C. | Yield % |
| Fluorenone perester (Formula IV) | $2.73 \times 10^2$ | 102–104 | 79 |
| Anthracene perester (Formula V) | $8.3 \times 10^3$ | 118–119 | 68 |
| Pyrene ketone perester (Formula II) | $1.0 \times 10^4$ | 122 | 65 |
| Pyrene ester perester (Formula III) | $1.82 \times 10^4$ | 107–109 | 80 |

Uv spectra for the peresters synthesized are shown in FIG. 1.

In every respect, the compounds reflect the photochemistry and the spectroscopy of the parent chromophore except that they are coupled to a tert-butyl perester functionality, either conjugated directly, or insulated by at least one methylene group included in the molecule. For these peresters to be useful photoinitiators they must absorb a light quantum and convert the derived energy to a bond homolysis reaction producing a tert-butoxy and an aryloxy free radical pair. G. Sosnovsky, *Free Radical Reactions in Preparative Organic Chemistry*, Mac Millan, New York, (1964); C. Ruchardt, *Angew Chem. Intern. Edt.* 9, 930 (1970).

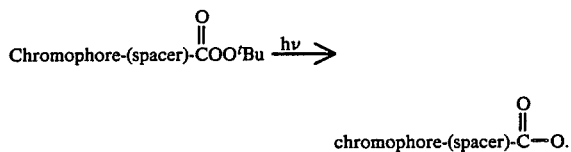

The ability of the photoinitiators in Table 1 to produce free radicals which initiate vinyl polymerization was studied by measuring the rate of polymerization of methyl methacrylate and styrene under identical conditions of light intensity, initiator concentration, monomer concentration and temperature. The conversion versus time curves for the photopolymerization of methyl methacrylate using these initiators are given in FIG. 2. As is shown in FIG. 2, the rate of MMA photopolymerization decreases in the following seqeuence of perester structure: fluorenone>pyrene ketoneZ>pyrene ester>anthracene.

Figure 3:
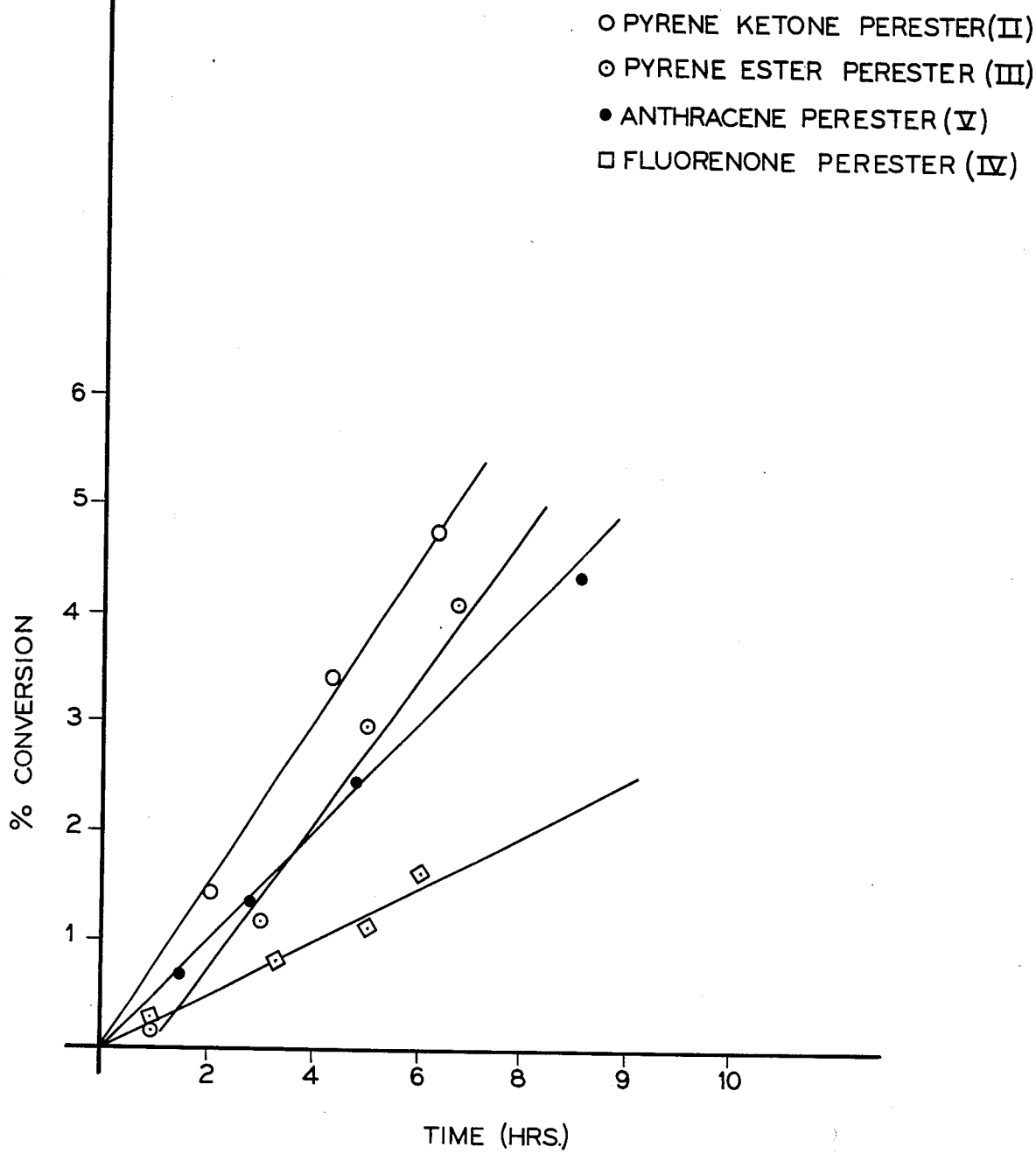
FIG. 3 is a graph showing photopolymerization of styrene (bulk) initiated by various peresters.

The photoinitiation of styrene initiated by each of these peresters was carried out similarly and is shown in FIG. 3. The rate of styrene photopolymerization decreased in the following order: pyrene ketone>pyrene ester>anthracene>fluorenone.

Figure 2:
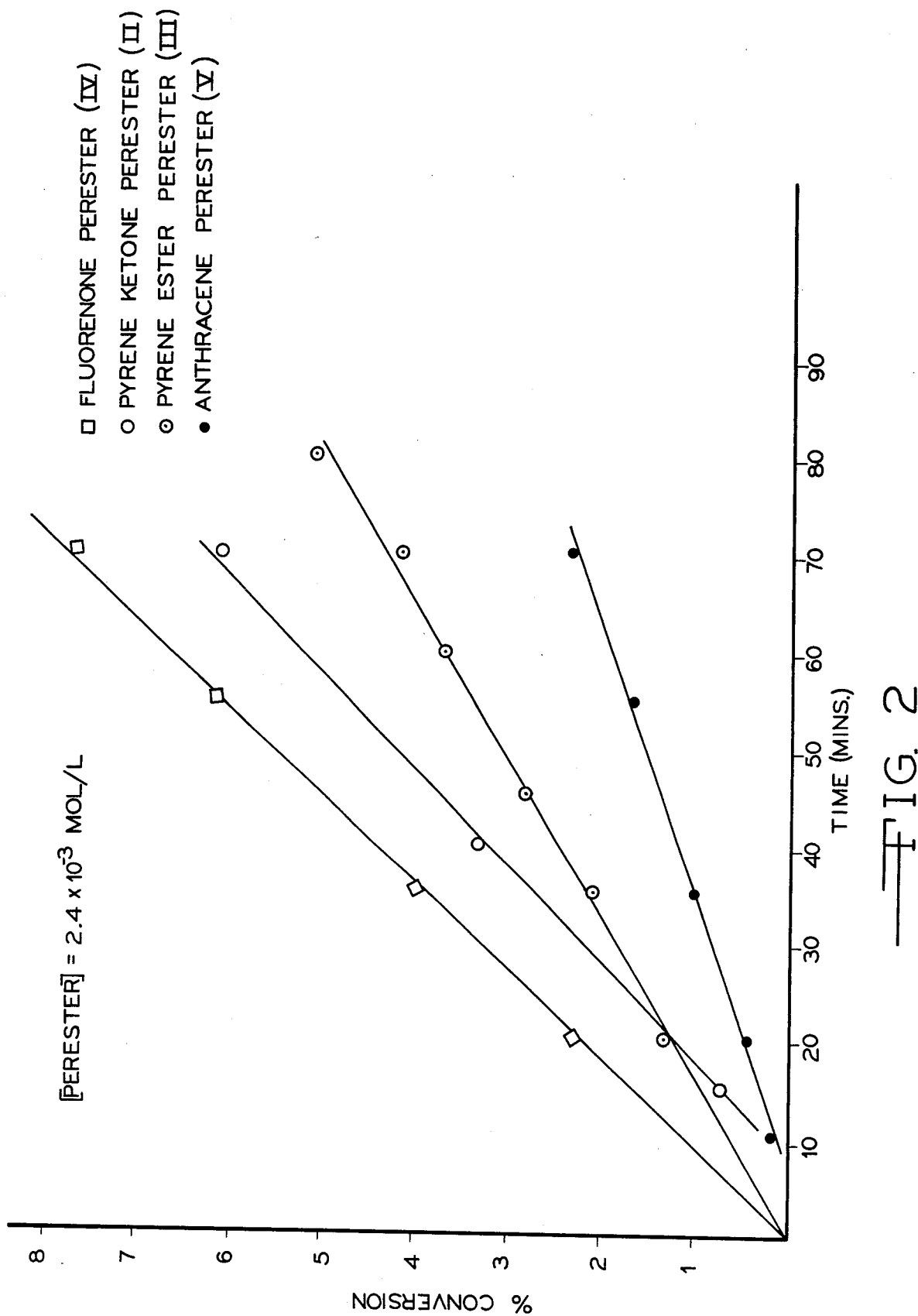
FIG. 2 is a graph showing photopolymerization of MMA (bulk) initiated by various peresters.

It is clear from FIG. 2 and FIG. 3 that the reactivity order of these aromatic peresters depends on the type of monomer being polymerized. Thus in the polymerization of MMA, the fluorenone perester, Formula IV, is the fastest, whereas in the polymerization styrene, it is the slowest. The rates of polymerization—at identical times for the two monomers, MMA and styrene, are compared in Table 2.

TABLE 2

Photo Polymerization (Bulk) of Vinyl Monomers Initiated by Various Peresters

| Initiator | After 60 mins. MMA Rp mol $1^{-1}$ sec$^{-1}$ | After 3 hrs. Styrene Rp mol $1^{-1}$ sec$^{-1}$ |
|---|---|---|
| Pyrene ester perester (Formula III) | $1.1 \times 10^{-4}$ | $1.95 \times 10^{-5}$ |
| Pyrene ketone perester (Formula II) | $1.54 \times 10^{-4}$ | $2.44 \times 10^{-5}$ |
| Fluorenone perester (Formula IV) | $1.92 \times 10^{-4}$ | $9.8 \times 10^{-6}$ |
| Anthracene perester (Formula V) | $5.63 \times 10^{-5}$ | $1.22 \times 10^{-5}$ |

Effects of Monomer and Perester Concentration on the Polymerization Rate

Figure 4:
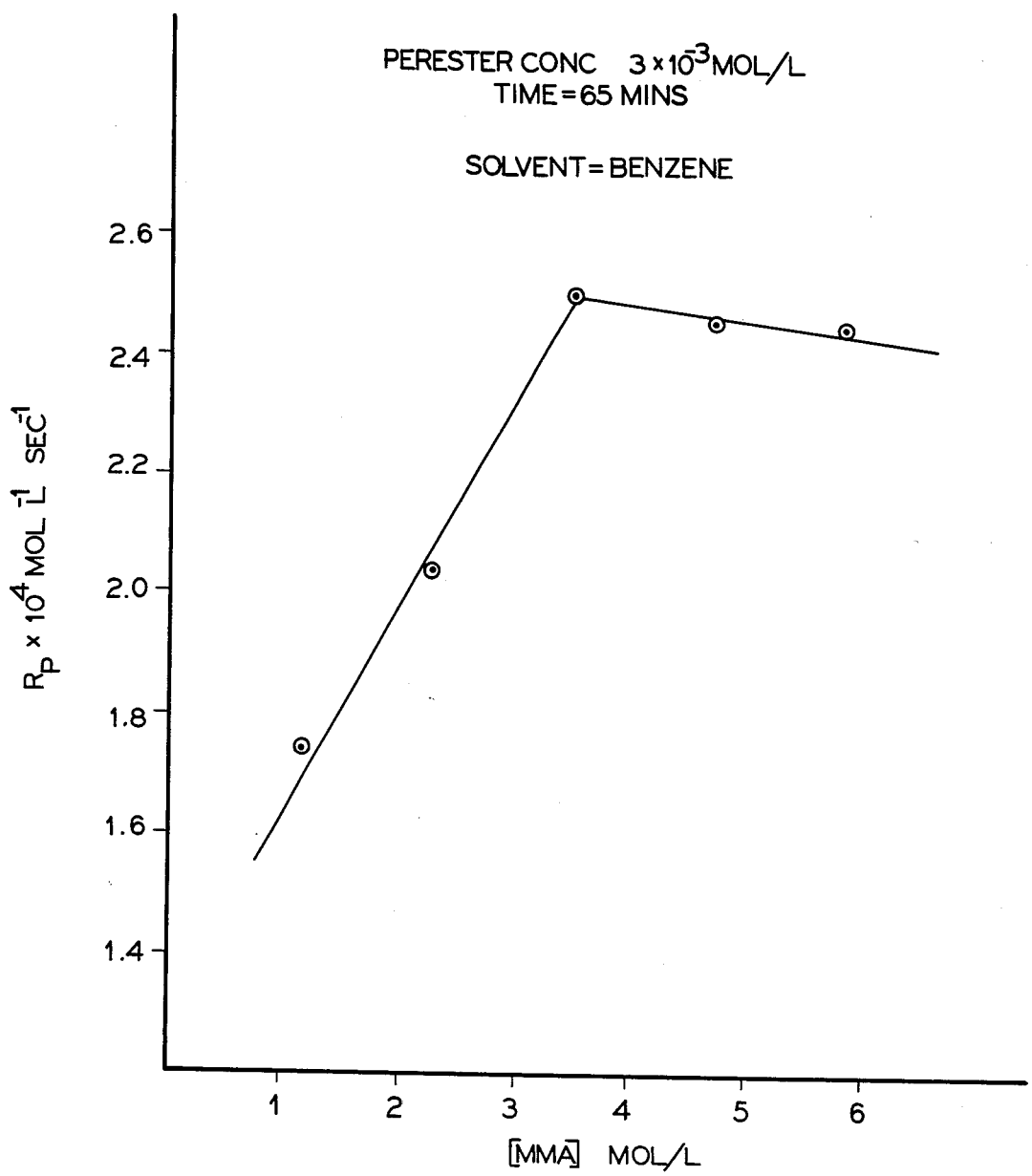
FIG. 4 is a graph showing photopolymerization of MMA initiated by fluorenone perester (Formula IV).

The relationship between the rate of polymerization, Rp, and the concentration of the monomer is a function of both the structure of the initiator and the monomer being polymerized. Thus the Rp of MMA with fluorenone perester, Formula IV, as the initiator increases to a maximum as the monomer concentration is increased (to about 3.5M in benzene) and then levels off, as seen in FIG. 4.

Figure 5:
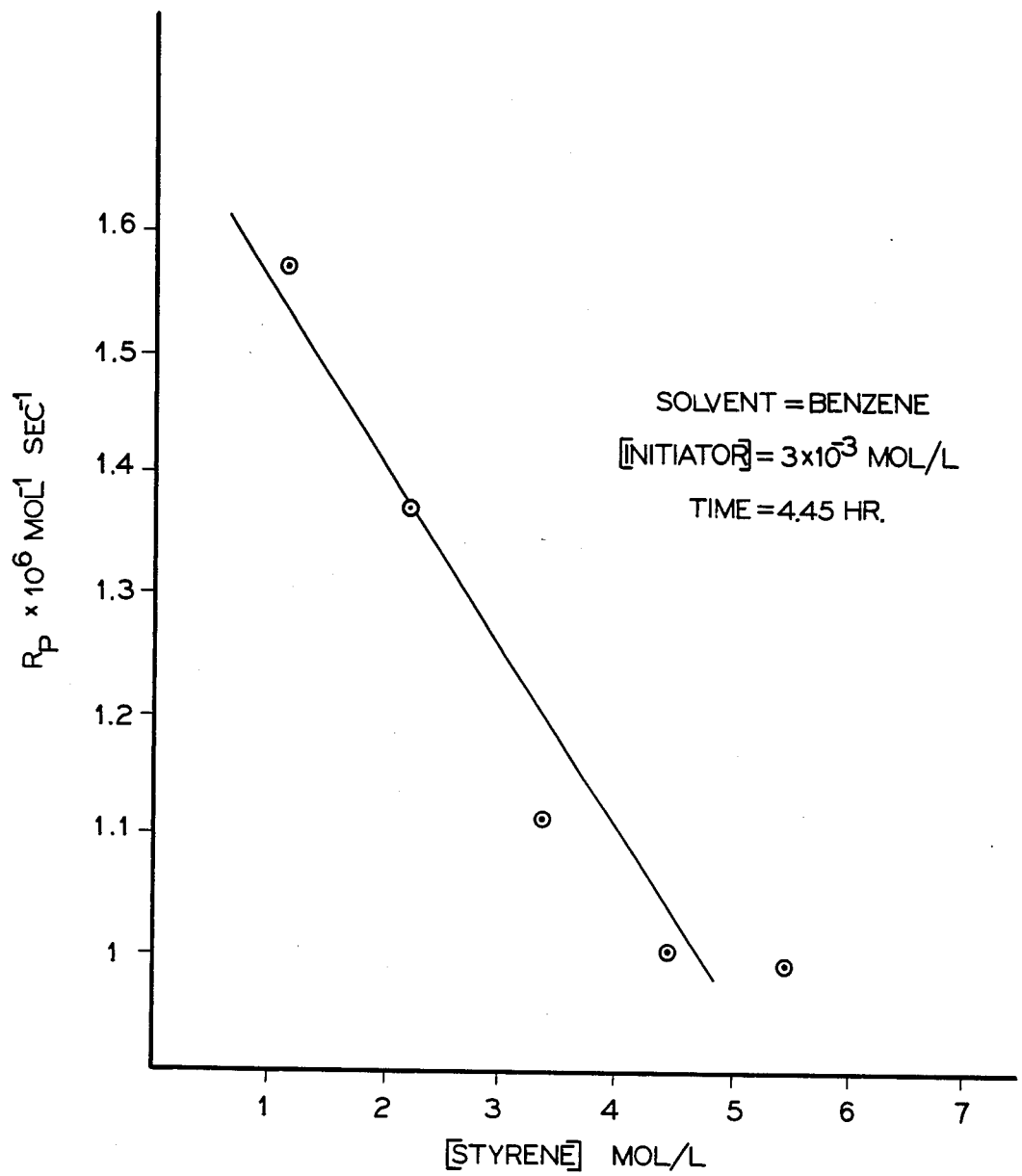
FIG. 5 is a graph showing photopolymerization of styrene initiated by fluorenone perester (Formula IV).

For styrene photopolymerization utilizing the same initiator, the concentration of styrene increases the rate of polymerization decreases, as seen in FIG. 5.

In this instance either the excited state of the initiator is quenched by the monomer, or the monomer reacts with the initiator before bond homolysis occurs.

Figure 6:
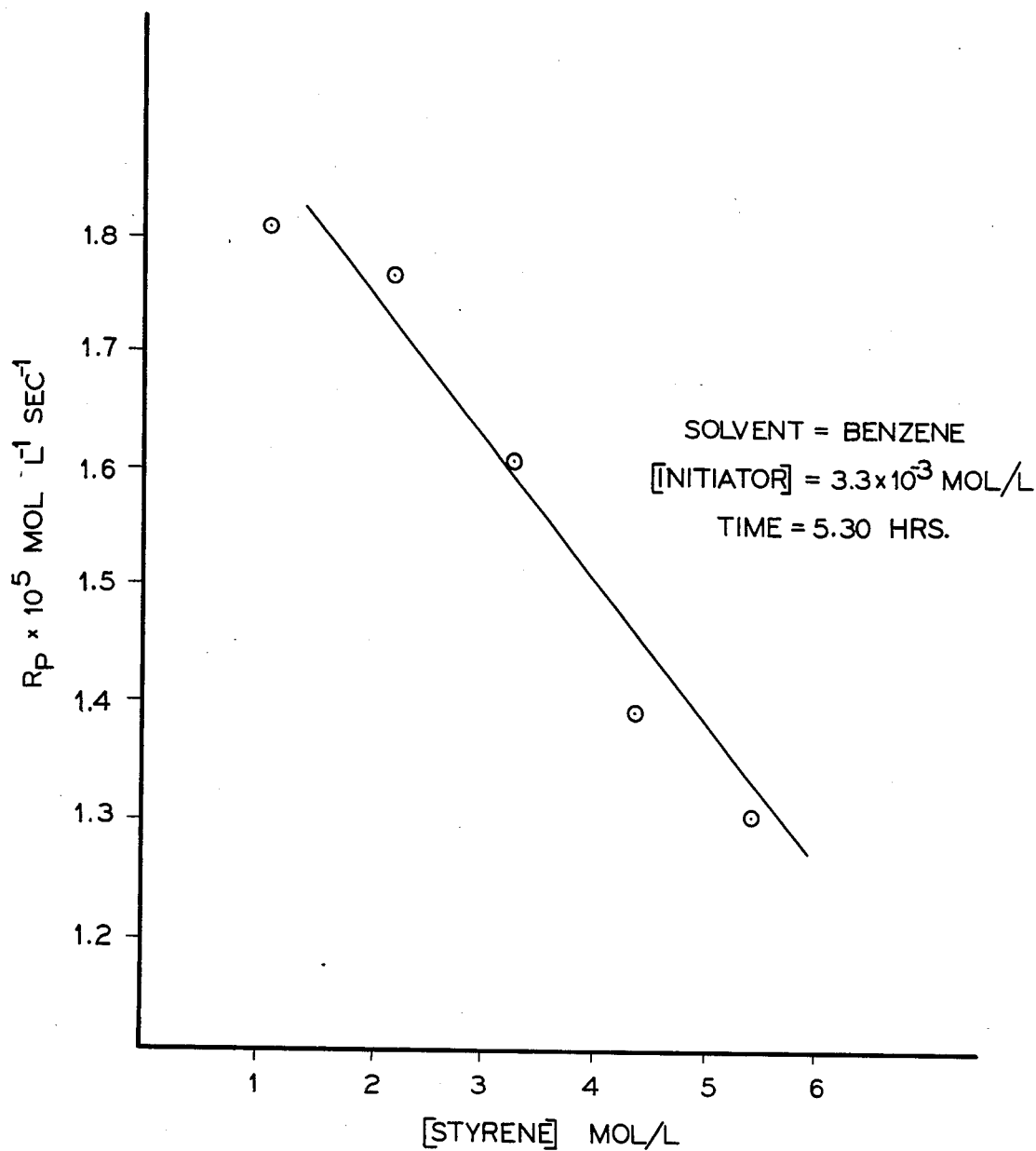
FIG. 6 is a graph showing photopolymerization of styrene by pyrene ketone perester (Formula II).

Formula II and Formula III peresters present test cases by means of which the localization of energy in the excited state is assessed. The keto pyrene perester, Formula II, is quenced by styrene or at least the rate of polymerization decreases as the styrene concentration is increased, as seen in FIG. 6.

Figure 7:
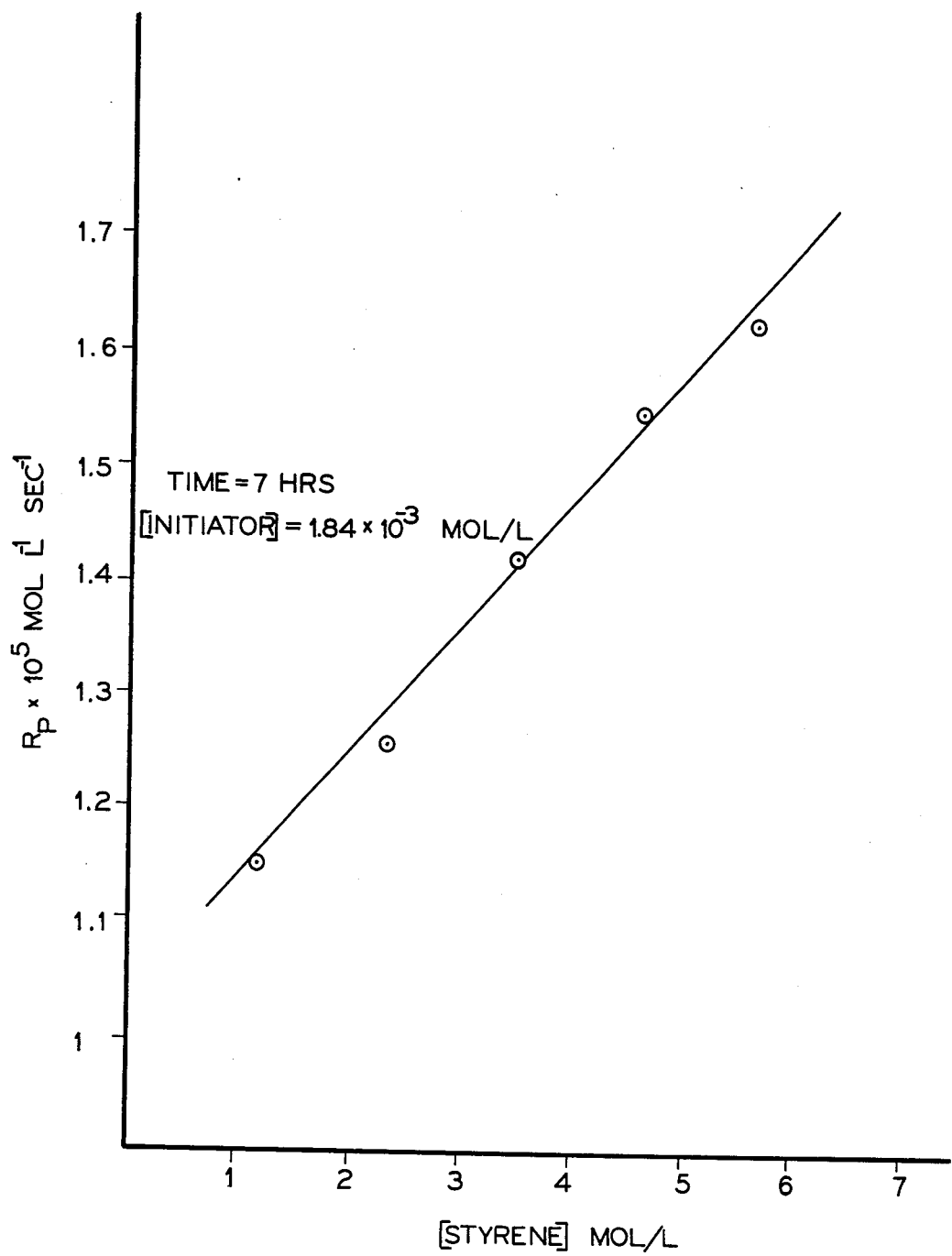
FIG. 7 is a graph showing dependence of the photopolymerization rate (Rp) of styrene on the monomer concentration in benzene for pyrene ester perester (Formula III).

The non-ketonic pyrene photoinitiator, Formula III, behaves more normally with the rate of styrene polymerization actually increases with concentration of monomer when it is used, as seen in FIG. 7.

Styrene solutions of the non-ketonic pyrene initiator, Formula III, fluoresce while being irradiated in the monomer (styrene or MMA) for the purpose of studying them as photoinitiators, while the ketonic pyrene systems (Formula II) are non-emitting under identical conditions.

Figure 8:
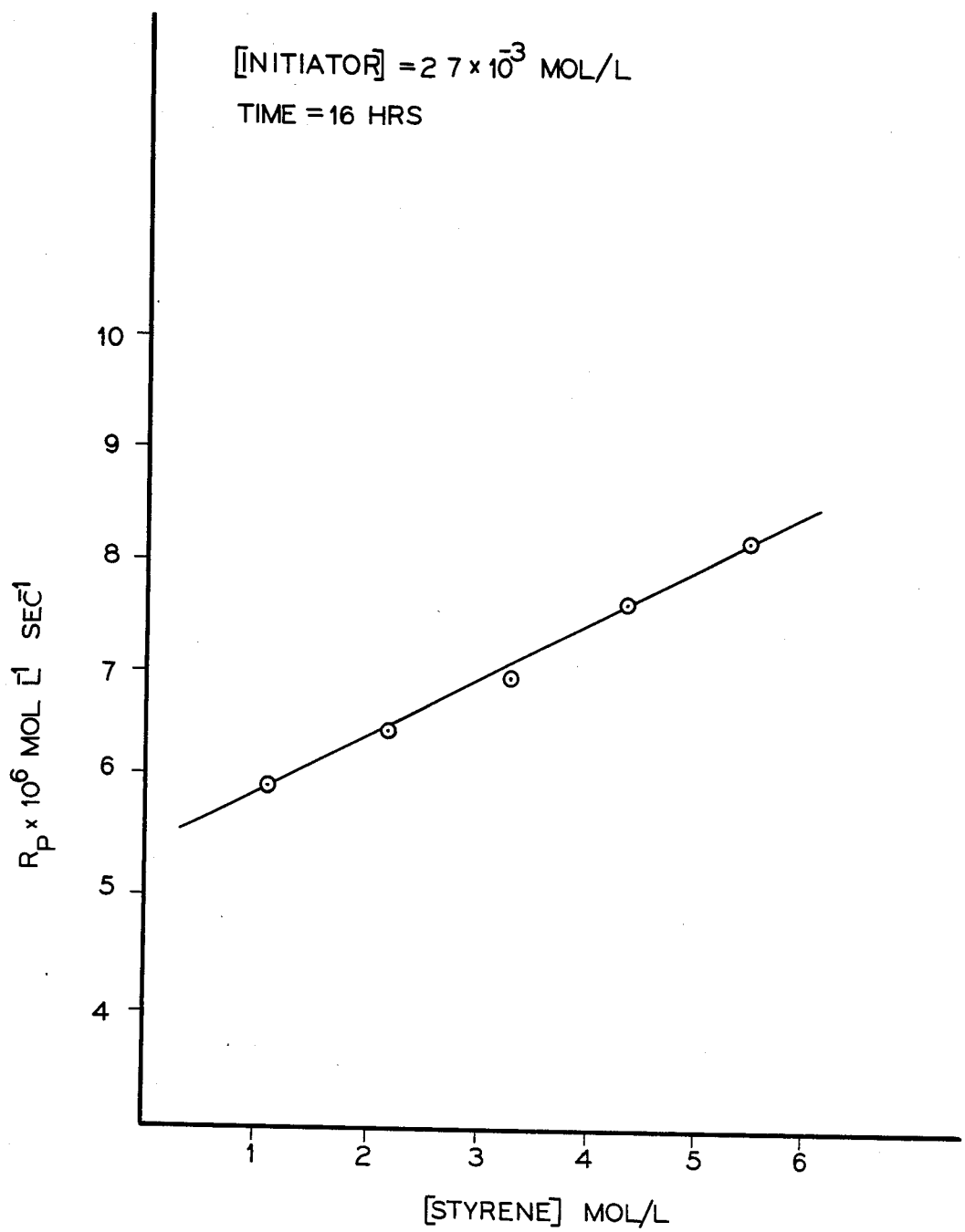
FIG. 8 is a graph showing dependence of the photopolymerization rate (Rp) of styrene on the monomer concentration for anthracene perester (Formula V).

FIG. 8 shows the rate of photopolymerization of styrene as a function of styrene concentration initiated by another $\pi$-$\pi$* photoinitiator, the anthracene derivatives, Formula V. As in the case of the pyrene perester, Formula III, the anthracene system is not quenched by styrene and the Rp increases with increasing styrene concentration.

Figure 9:
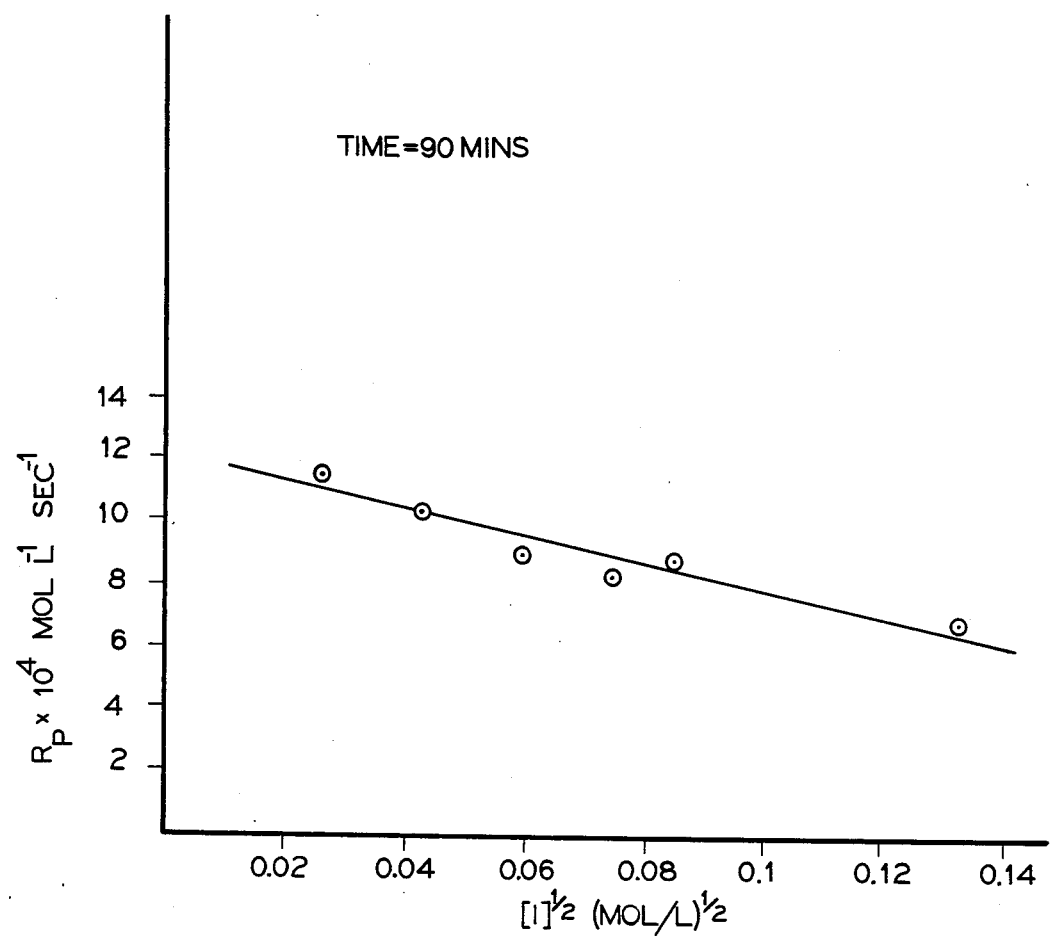
FIG. 9 is a graph showing dependence of the photopolymerization rate (Rp) of MMA on the initiator concentration for pyrene ester perester (Formula III).

The effect of initiator concentration on the rate of polymerization is determined by the termination step of the radical chain as described by S. Gupta, I. Gupta and D. C. Neckers, *J. Poly. Sci., Poly. Chem. Ed.* 19, 103 (1981), and is half order in initiator when termination is bimolecular in chain fragments. The rate, as a function of initiator concentration, also is a function of self-quenching of initiator excited states. Thus, the way the rate of polymerization of MMA could decrease as a function of pyrene perester concentration, as seen in FIG. 9, is if the excited state of the perester were quenched either by another perester ground state, or by a perester residue present in a polymer chain. Increasing the initiator fragments in the system increases the possibility of chromophore self-quenching and decreases the rate of initiation at higher concentrations of photoinitiator.

Effect of Monomer and Perester Concentration on the Molecular Weight of the Polymer Table 3 and Table 4 show the effect of polymerization time and the structure of the aromatic perester photoinitiator on the molecular weight of the derived polymer, both in the case of methyl methacrylate and styrene.

TABLE 3

Photopolymerization of MMA (Bulk) Initiated by Various Peresters Molecular Weight Dependence on Initiator Structure and Polymerization Time

| Initiator | Polymerization Time (Mins.) | Mn (average) |
|---|---|---|
| Pyrene ketone perester (Formula II) | 40 | $1.7 \times 10^4$ |
|  | 70 | $2.23 \times 10^4$ |
| Fluorenone perester (Formula IV) | 10 | $3.15 \times 10^4$ |
|  | 25 | $3.87 \times 10^4$ |
|  | 40 | $4.15 \times 10^4$ |
|  | 70 | $5.0 \times 10^4$ |
| Anthracene perester (Formula V) | 20 | $1.0 \times 10^5$ |
|  | 35 | $1.3 \times 10^5$ |
|  | 70 | $7.9 \times 10^5$ |
| Pyrene ester perester (Formula III) | 35 | $5.86 \times 10^4$ |
|  | 45 | $7.0 \times 10^4$ |
|  | 60 | $7.9 \times 10^4$ |

TABLE 3-continued

Photopolymerization of MMA (Bulk) Initiated by Various Peresters Molecular Weight Dependence on Initiator Structure and Polymerization Time

| Initiator | Polymerization Time (Mins.) | Mn (average) |
|---|---|---|
| | 100 | $1.58 \times 10^5$ |

TABLE 4

Photopolymerization of Styrene (Bulk) Initiated by Various Peresters

| Initiator | Photopolymerization Time (Hours) | Mn |
|---|---|---|
| Pyrene Ester Perester (Formula III) | 1 | $2.5 \times 10^4$ |
| | 3.15 | $5.6 \times 10^4$ |
| | 5 | $6.3 \times 10^4$ |
| Fluorenone Perester (Formula IV) | 3 | $1.17 \times 10^5$ |
| | 6 | $1.12 \times 10^5$ |
| | 10.15 | $1.05 \times 10^5$ |
| Pyrene Ketone Perester (Formula II) | 4.20 | $2.5 \times 10^4$ |
| | 6.15 | $3.1 \times 10^4$ |
| | 10.30 | $1.4 \times 10^5$ |
| Anthracene Perester (Formula V) | 1.30 | $1.78 \times 10^5$ |
| | 3 | $2.3 \times 10^5$ |
| | 4.50 | $2.8 \times 10^5$ |

Figure 10:
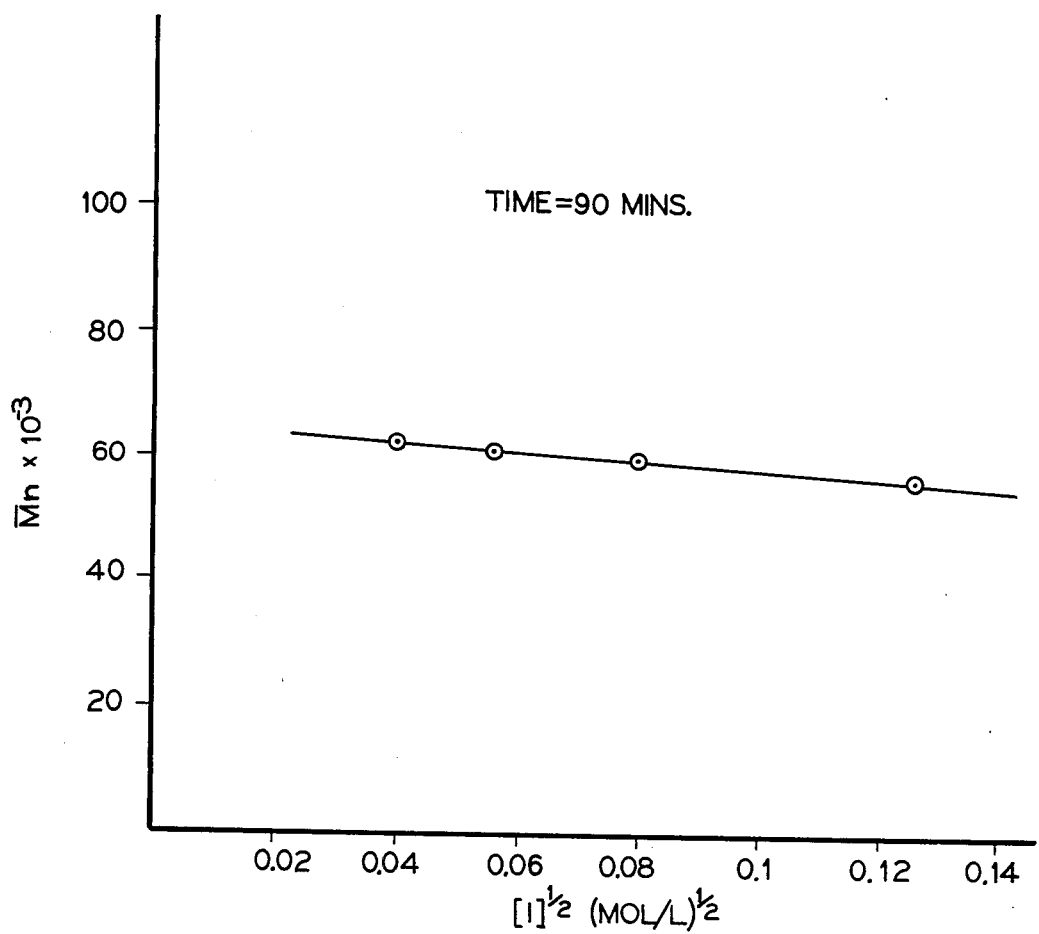
FIG. 10 is a graph showing dependence of the molecular weight of the polymer on the initiator concentration for photopolymerization of MMA (bulk) initiated by pyrene ester perester (Formula III).

FIG. 10 shows that the molecular weight of the MMA formed from one of the aromatic photoinitiators is inversely proportional to the square root of the initiator concentration.

Figure 11:
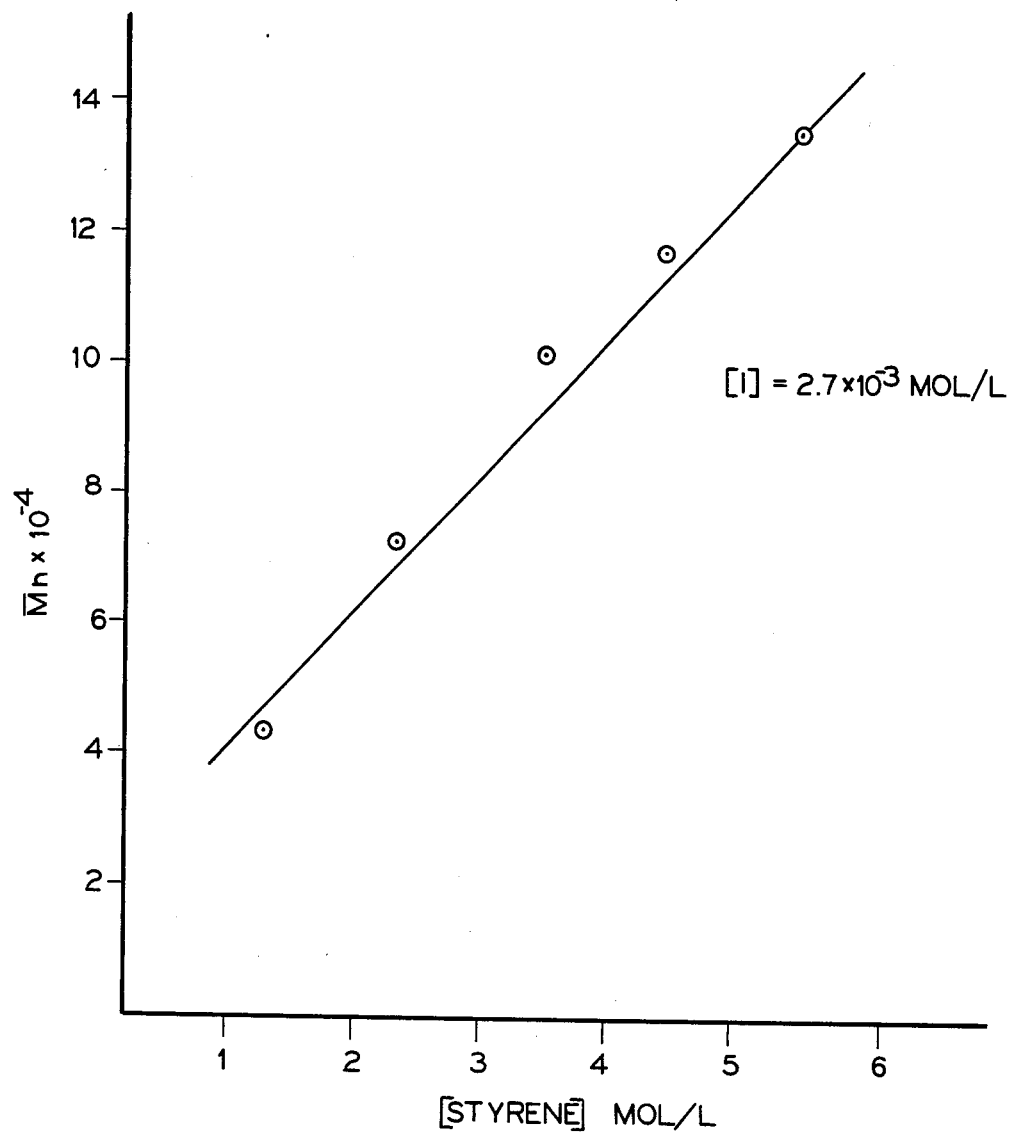
FIG. 11 is a graph showing dependence of the molecular weight of the polymer on the monomer concentration for photopolymerization of styrene initiated by anthracene perester (Formula V).

FIG. 11 shows that the molecular weight of polystyrene formed from the anthracene perester photoinitiation increases as the monomer concentration increases.

Figure 12:
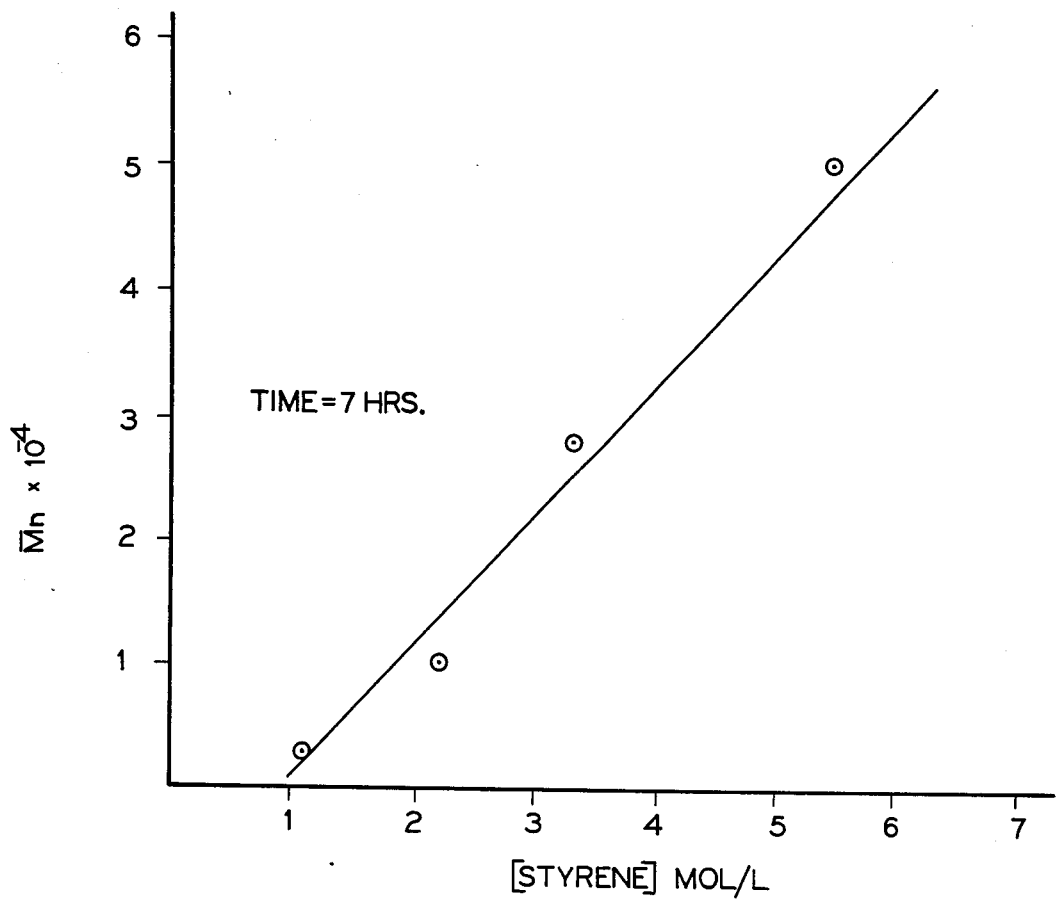
FIG. 12 is a graph showing photopolymerization of styrene bulk initiated by pyrene ester perester (Formula III).

FIG. 12 shows the same relationship between styrene concentration and its polymer molecular weight where the initiator is the pyrene Formula III ester system.

It is an anomaly that though the rate of polymerization of styrene with the Formula V initiator is 1 to 2 orders of magnitude larger than for the Formula III initiator, the Mn of polymers deriving from the Formula V initiator are higher than with the Formula III. The polycyclic aromatic hydrocarbons also serve as radical quenchers. Thus, these peresters also participate in non-initiating reactions with growing radical chains. This is demonstrated by polymerization on the appropriate monomer thermally with AIBN in the presence of the Formula II, III, IV and V initiators. All monomers except Formula IV terminate radical chains sufficiently to decrease the rate of polymerization by as much as 10% when present in concentrations equivalent to those of the AIBN initiator at 70° C.

To test the thermal stability of the perester, attempts are made to measure decomposition rates at 80° C. in benzene. While $Bz_2O_2$ shows a decomposition rate comparable to the literature value, the peresters do not decompose at all at 80° C. The thermal rates of decomposition in the dark are measured at 110° C. in chlorobenzene and are comparable in value to the rates of decomposition of substituted tert-butyl perbenzoates.

The peresters all provide efficient photochemical sources of free radicals. Important from a practical view is that their photodecomposition is controllable (effectively it can be tuned) by the absorption characteristics of the absorbing chromophore.

EXAMPLE 3

Synthesis of a photoinitiator, of a bisperester utilizing the same design, p'-tert-butylperoxycarbonyl-p-benzoyl-tert-butyl perbenzoate Formula VI:

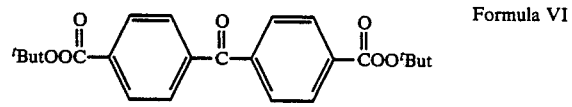

Formula VI

The triplet energy of the benzophenone triplet state is approximately twice that of the bond dissociation energy of the O—O bond of the perester. Light absorption by the carbonyl group leads to dissociation of both peresters and a photoinitiator which is substantially more efficient than p-benzoyl-tert-butyl perbenzoate. When Formula VI is used as a photoinitiator for methyl methacrylate, it is more efficient than the monoperester benzophenone tert-butyl perbenzoate and, as measured by the rate of monomer polymerization, it also decomposes with a higher quantum yield.

Synthesis of 4-Benzoyl(4'-tert-Butylperoxycarboxyl) tert-Butyl Perbenzoate (Formula VI)

p, p'-Dimethylbenzophenone (7.0 g, 0.033 mol), sodium dichromate (27.0 g, 0.10 mol), and 120 mL of water were placed in a 500-mL round-bottomed flask equipped with an unsealed mechanical stirrer. Concentrated sulfuric acid (75 mL, 1.4 mol) was added by means of a dripping funnel over a period of 30 min. After the addition of the acid was complete a reflux condenser was attached and the mixture heated to gentle boiling for 4 h. After cooling, the reaction mixture was added to 500 mL of ice water, filtered, and washed with copious amounts of cold water. The resulting crude acid was then transferred to a 1-L beaker, 200 mL of water containing 10 mL of sulfuric acid added, and the mixture digested on water bath for a short period of time to remove the excess chromium salts. After a subsequent filtration, the crude acid was purified by the addition of dilute NaOH, filtered to remove undissolved solids, acidified, and filtered. For structure confirmation, the purified acid, which has a melting point of which agreed with that reported in Koelsch, et al., *J. Am. Chem. Soc.*, 67, 2041 (1945).

The compound (Formula VII), benzophenone p, p'-dicarboxylicacid,

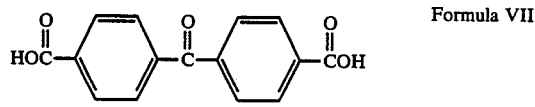

Formula VII was converted to the diacid chloride (Formula VIII) by refluxing overnight with an excess of thionyl chloride. After removal of the excess thionyl chloride in vacuo and recrystallization of the product from hexane/dichloromethane, 85% of the dichloride (mp 133° C.; lit. 132-133) was obtained.

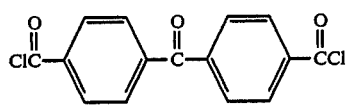

Formula VIII

The bisperester (Formula VI) was obtained as follows: Formula VIII (0.74 g, 0.0024 mol) was dissolved in 40 mL of dry ether and 20 mL of dichloromethane. The reaction mixture was stirred mechanically at room temperature for 15 min and cooled with an ice/salt bath. Tert-butyl hydroperoxide (0.5 mL, 0.005 mol) in 2 mL benzene and triethylamine (07 mL, 0.005 mol) in 10 mL of ether were added slowly in the dark. The reaction mixture was held at ice temperatures for two hours, then allowed to warm to room temperature, and the solvent removed at room temperature in vacuo. The product was purified by column chromatography in the dark on silica gel. The crude bisperester was dissolved in dichloromethane and then eluted with dichloromethane (recovered yield 45%). The purified compound (mp 114° C.) gave one spot on TLC (dichloromethane), ε366 nm=170 l/mol; IR: 1680, 1770 cm$^{-1}$; NMR: 1.05 s (t-but), aromatic $A_2B_2$.

The rate of decomposition of the bisperester was studied by irradiation in benzene as per the techniques we have reported previously; ε366 nm=1.74×10$^4$ L/ms).

Figure 13:
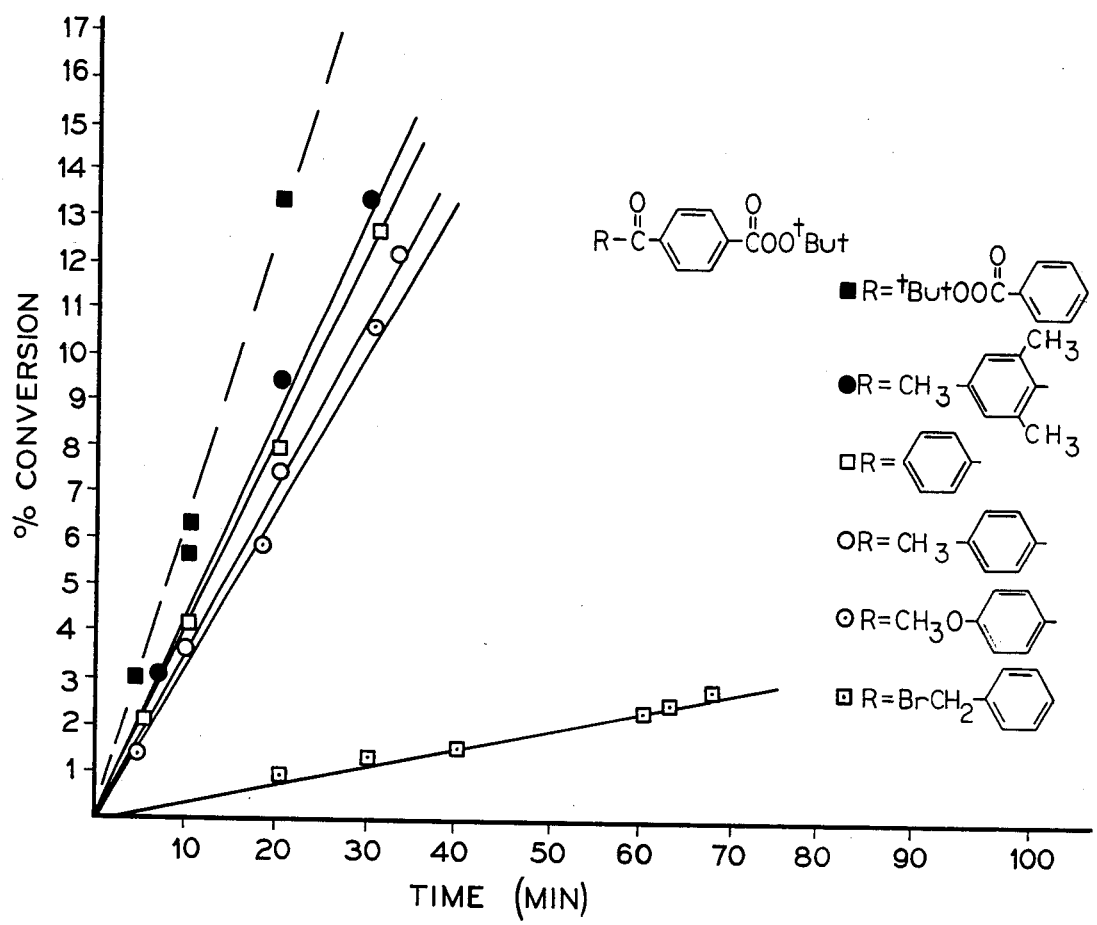
FIG. 13 is a graph showing photopolymerization by methylmethacrylate (MMA) (bulk) initiated by various peresters.

The physical and spectral parameters of import for each of the studied peresters are outlined in Table 5 below.

case of one of the peresters, this might not necessarily be the most ideal wavelength at which it should be irradiated. The conversion/time curves for photopolymerization of MMA with the various peresters are compared in FIG. 13. The bisperester (Formula VI) is a better initiator than the corresponding monoperester even though the spectral characteristics of the initiator chromophores are quite the same. Some differences appear in the monoperesters as a function of the substituent. The rates of polymerization with the substituted initiators decreased, as shown in FIG. 13.

Figure 14:
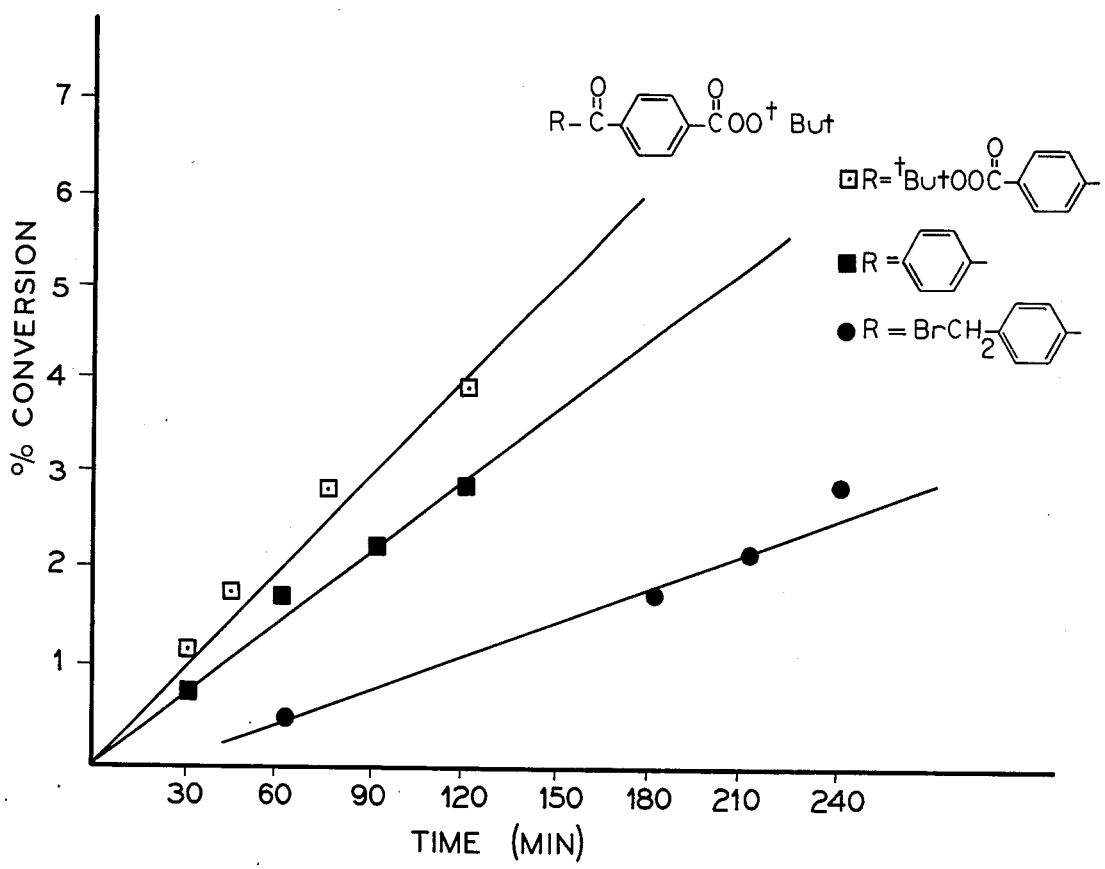
FIG. 14 is a graph showing photopolymerization of styrene (bulk) initiated by various benzophenone peresters.

The photopolymerization of styrene, initiated by each of the peresters derived from benzophenone, was carried out similarly. FIGS. 13 and 14 compare benzophenone-type peresters as photoinitiators for the monomers MMA and styrene. As observed from the MMA data, even very different monoperesters give a similar rate of polymerization. The diperester, on the other hand, gives the highest rate, while the p-bromomethyl perester is much the slowest.

The polymerization of styrene initiated by each of the benzophenone derivatives is much slower than is the polymerization of MMA under the same conditions. This is due in part to the fact that the triplet energy of styrene is about 62 Kcal/mol and therefore lies much below the $E_t$ of the benzophenone chromophore. Since energy transfer is generally diffusion controlled, in bulk styrene monomer a high percentage of the excited states formed by light absorption into the benzophenone chromophore are quenched before the energy gets to the perester bond and dissociation can take place. MMA is

TABLE 5

Spectral Properties of Specific Peresters

| Compound | φ | $E_t$ (kcal/mol) | ε 366 nm ($CH_2Cl_2$) |
|---|---|---|---|
| Ph-C(O)-C6H4-COO$^t$But | 0.94 | 67.7 | 121.5 |
| $^t$ButOOC-C6H4-C(O)-C6H4-COO$^t$But (Formula IV) | 1.2 |  | 170 |
| 2,4,6-(CH$_3$)$_3$C6H2-C(O)-C6H4-COO$^t$But |  |  | 127.6 |
| CH$_3$O-C6H4-C(O)-C6H4-COO$^t$But | 0.75 |  | 216.4 |
| CH$_3$-C6H4-C(O)-C6H4-COO$^t$But | 0.80 | 67.4 | 108.1 |
| BrCH$_2$-C6H4-C(O)-C6H4-COO$^t$But |  |  | 10.7 |

The polymerization of methyl methacrylate was carried out with the initiators in Table I under identical conditions of concentration, light intensity, monomer concentration, and temperature. All irradiations were carried out with a mercury arc source equipped with filters to isolate the 366-nm line to prevent direct polymerization of the monomer even though, in at least the also more reactive than styrene. For example, the chain transfer constant with carbon tetrachloride for styrene is 9.2×10$^{-3}$ l/mol s for styrene, but 0.5×10$^{-3}$ l/mol s for MMA at 60° C. While $k_p$ for MMA=315 l/mol s, the $k_p$ of styrene is 74±5 l/mol s at 25° C.

Irradiation of the p-benzoyl-tert-butyl perbenzoate produces three different radicals: the benzoyloxy radical, the aryl radical, and the tert-butoxy radical. Continued irradiation of the formed polymer increases molecular weight by dimerization reations deriving from the reactions of the benzophenone carbonyl function with the polymer. There is also some effect of initiator structure on the molecular weight of the polymer formed and the polymerization rate under identical conditions. This is shown by the data in Table 6.

-continued

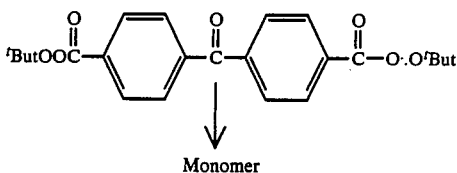

↓

Monomer

TABLE 6

Rate of Photopolymerization Rp of MMA (Bulk) Initiated by Various Benzophenone Peresters; Time 30 min, Peresters Concentration $2.4 \times 10^{-3}$ mol/l

| Initiator | $R_p$ (l mol$^{-1}$s$^{-1}$) | $M_n$ |
|---|---|---|
| 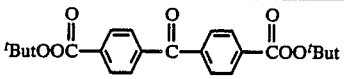 Formula IV | $1.14 \times 10^{-3}$ | $2.5 \times 10^4$ |
| 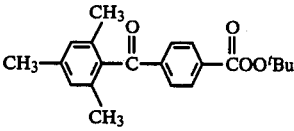 | $7.9 \times 10^{-4}$ | $3.15 \times 10^4$ |
| 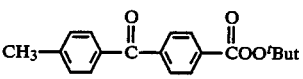 | $6.3 \times 10^{-4}$ | $4.67 \times 10^4$ |
| 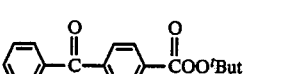 | $7.0 \times 10^{-4}$ | $1.61 \times 10^4$ |
| 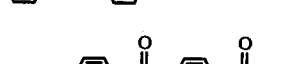 | $6.0 \times 10^{-4}$ | $2.33 \times 10^4$ |
|  | $9 \times 10^{-5}$ | $1.9 \times 10^5$ |

Figure 15:
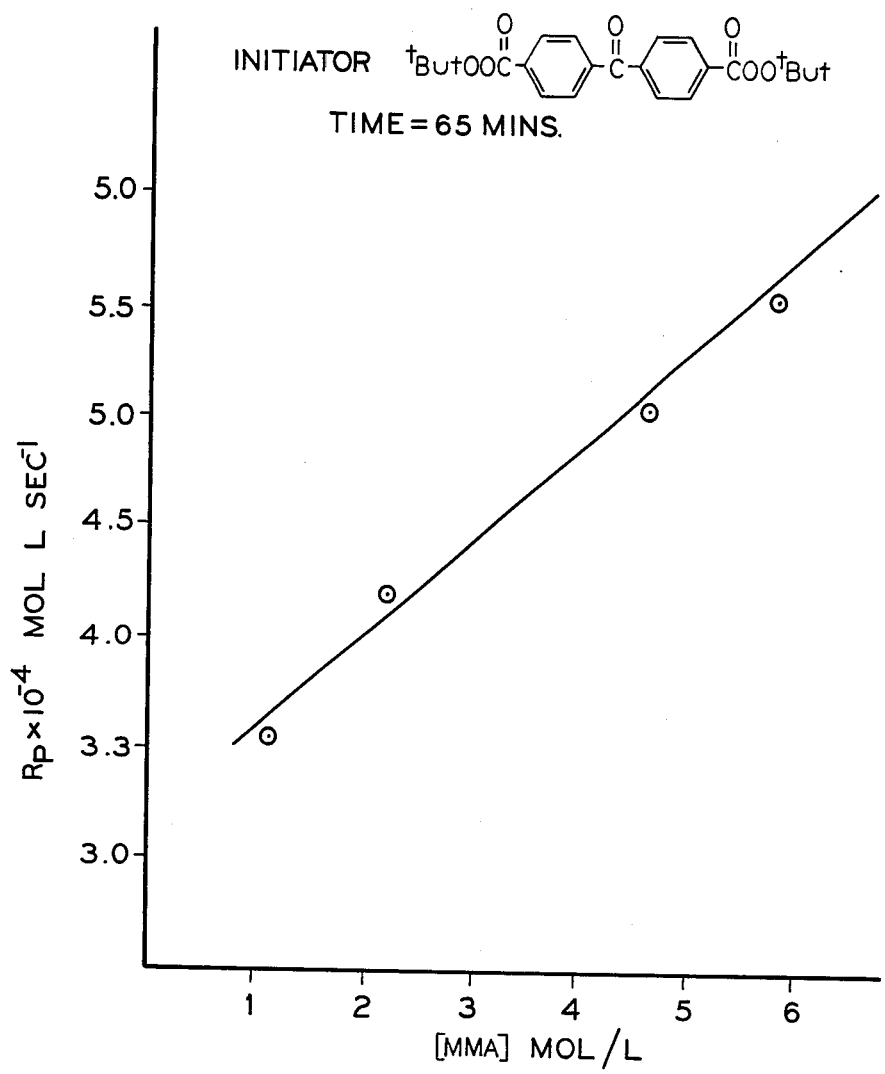
FIG. 15 is a graph showing dependence of the photopolymerization rate (Rp) of methylmethacrylate (MMA) on monomer concentration in benzene.
Figure 16:
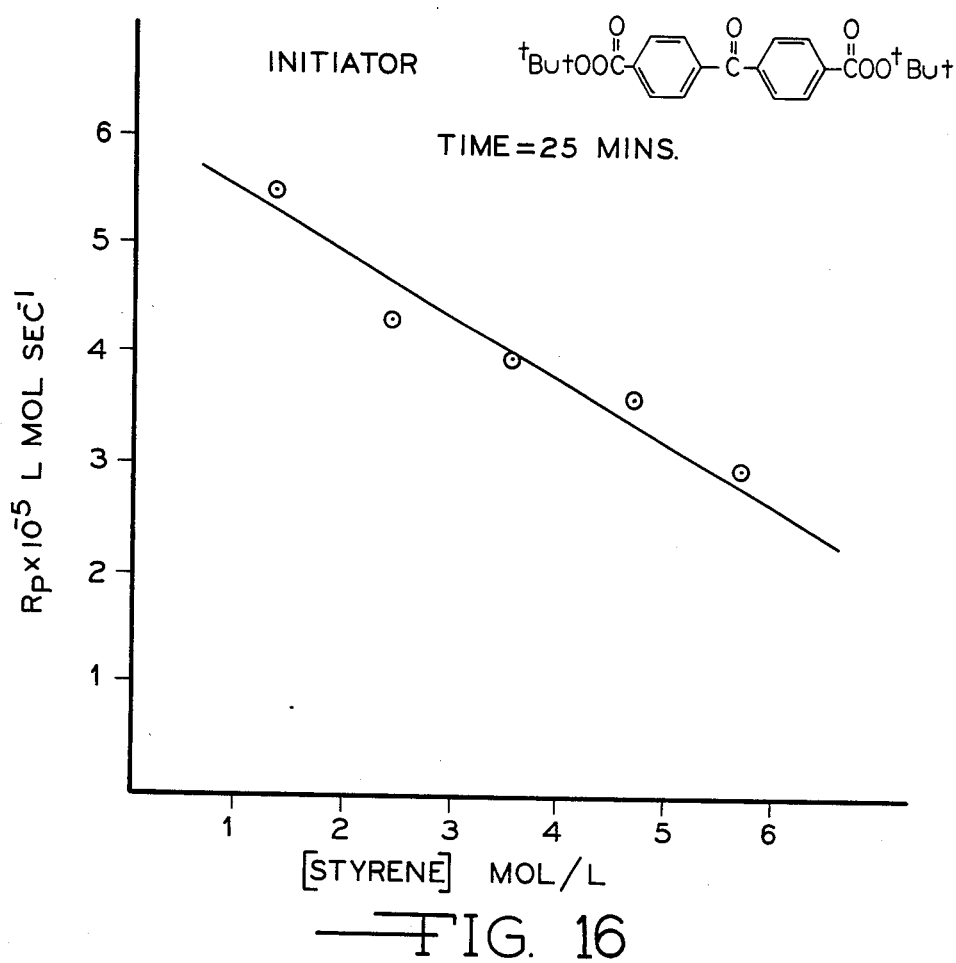
FIG. 16 is a graph showing dependence of the photopolymerization rate (Rp) of styrene or monomer concentration in benzene.

Effect of the Monomer and the Polymer Concentration on the Rate of Polymerization The relationship between the rate of polymerization Rp and the concentration of MMA in benzene is shown in FIG. 15 for the disperester. A linear plot was obtained for Rp vs. [M] with a slope of 0.43 with a range of monomer concentrations from 1-6 mol. The behavior of the diperester and p-benzoyl-tert-butyl perbenzoate were similar. FIG. 16 traces the effect of monomer concentration of Rp for styrene. Unlike the polymerization of MMA, whose rate increases with monomer concentration, the rate of styrene polymerization decreases with increasing concentration of the monomer. Just as with the monoperester, the triplet state of the diperester is also quenched by the aromatic monomer, styrene. This is explained by the following mechanism:

Formula VI $\xrightarrow{h\nu}$ VI* $\xrightarrow{\text{styrene}}$ VI + Styrene

↓

The lower rate of polymerization for reactions initiated by the bromomethyl perester (Formula IX)

Formula IX derives from the formation of radicals of different reactivity from that perester. Rather than dissociation of the perester O—O bond to form the incipient benozoyloxy radical and tert-butoxy radical, in the case of the p-bromomethyl perester, dissociation to the benzyl radical and bromine atom is preferred. These are both less reactive and rates of initiation therefore retarded. This observation is confirmed by product studies in this system, which indicate that the major products are bibenzyls with the perester function remaining intact. Photofragmentations of p-halobenzophenones have been the subject of numerous studies. p-Chloromethylbenzophenone, for instance, cleaves at the benzylic carbon-chlorine bond. See H. G. Heine, H. J. Rosenkranz and H. Rudolph, *Angew. Chem. Int.* Ed. English 11, 974 (1972). The products from this system is identical to those we are suggesting formed with the bromomethyl perester, e.g., (See Table 7 below).

TABLE 7

Thermal Polymerization of MMA Bulk at 70° C. (in the Dark)

| Initiator | $R_p$ (l mol$^{-1}$s$^{-1}$) |
|---|---|
| ${}^tBuOOC-\text{C}_6H_4-C(O)-C_6H_4-COO^tBu$ | $3.5 \times 10^{-5}$ |
| $C_6H_5-C(O)-C_6H_4-COO^tBu$ | $2.0 \times 10^{-5}$ |
| AIBN | $3.9 \times 10^{-4}$ |

$$C_6H_5-C(O)-C_6H_4-CH_2Cl \xrightarrow{h\nu} C_6H_5-C(O)-C_6H_4-CH_2Cl \rightarrow \text{Bibenzyls}$$

Figure 17:
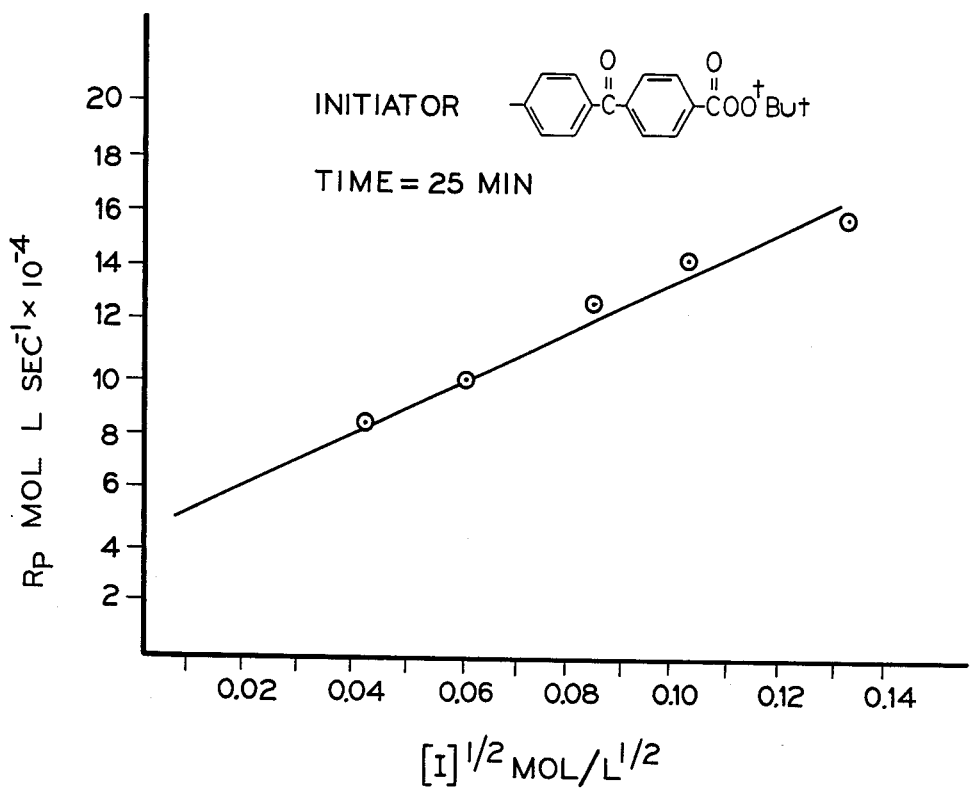
FIG. 17 is a graph showing the square-root dependence of the photopolymerization rate (bulk) (Rp) of methylmethacrylate (MMA) on initiator concentration.
Figure 18:
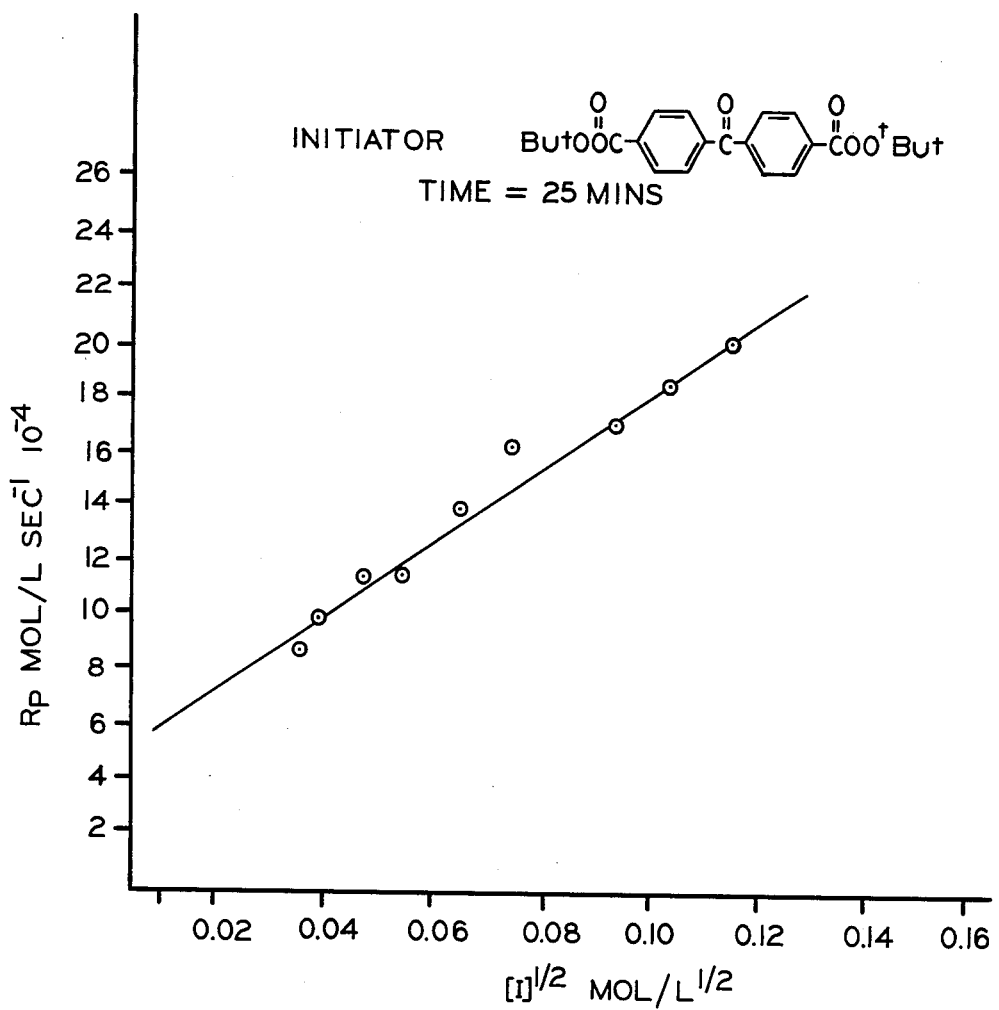
FIG. 18 is a graph showing the square-root dependence of the photopolymerization rate (Rp) (bulk) on the initiator concentration; monomer methylmethacrylate (MMA), solvent benzene.

The rate of polymerization is related to the initiator concentration by a square-root dependence. This is shown in FIG. 17 for the monoperester and in FIG. 18 for the bisperester. In both cases the monomer was MMA and the solvent was benzene.

The data in FIGS. 15–18 show that the polymerization rate is half order in photoinitiator and first order in monomer. At high monomer concentration, the rate of polymerization increases because all of the radicals formed from the initiator are used to initiate polymerization. At lower monomer concentration, radicals are wasted in recombination in the solvent cage or by termination of fragments outside the cage before they can initiate polymer formation.

Figure 19:
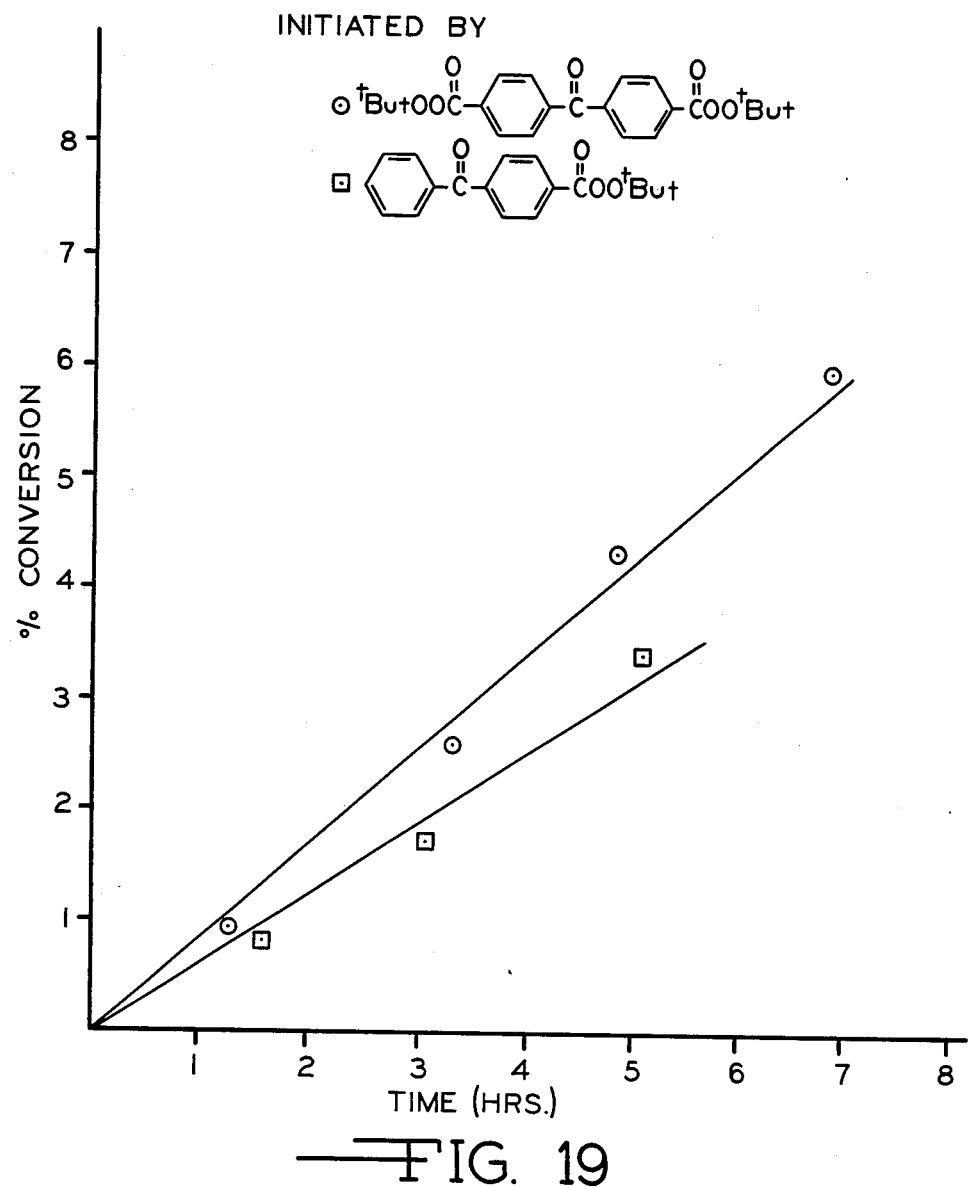
FIG. 19 is a graph showing thermal polymerization of styrene (bulk) at 70° C. in the dark.

The data for the monoperesters and the diperesters are shown in FIG. 19 with styrene as the monomer. The rates of polymerization are given by the data in Tables 7 and 8. In the thermal reaction, the molecular weight of the polymer is unaffected by reaction time and it decreass gradually as the concentration of the perester used for initiation is increased. This indicates that, in the thermal reaction, the perester acts normally and as a chain transfer reagent for the growing polymer chain, whereas in the photochemical reaction the initiator fragment can react as a crosslinking entity as long as the light remains on.

TABLE 8

Effect of Perester Structure on Rate of Polymerization of Styrene (Bulk) and the Molecular Weight of Polymer Obtained; [I] = 2.4 × 10$^{-3}$mol/l

| Initiator | Polymerization time (h) | $R_p$ (l mol$^{-1}$s$^{-1}$) × 10$^{-5}$ | $M_n$ × 10$^5$ |
|---|---|---|---|
| ${}^tBuOOC-C_6H_4-C(O)-C_6H_4-COO^tBu$ | 3.15 | 2.25 | 2.95 |
|  | 4.45 | 2.6 | 2.95 |
|  | 6.45 | 2.56 | 2.95 |
|  | 1.30 | 1.65 | 2.95 |
| $C_6H_5-C(O)-C_6H_4-COO^tBu$ | 3.00 | 1.65 | 2.8 |
|  | 5.00 | 1.97 | 3.0 |

Figure 20:
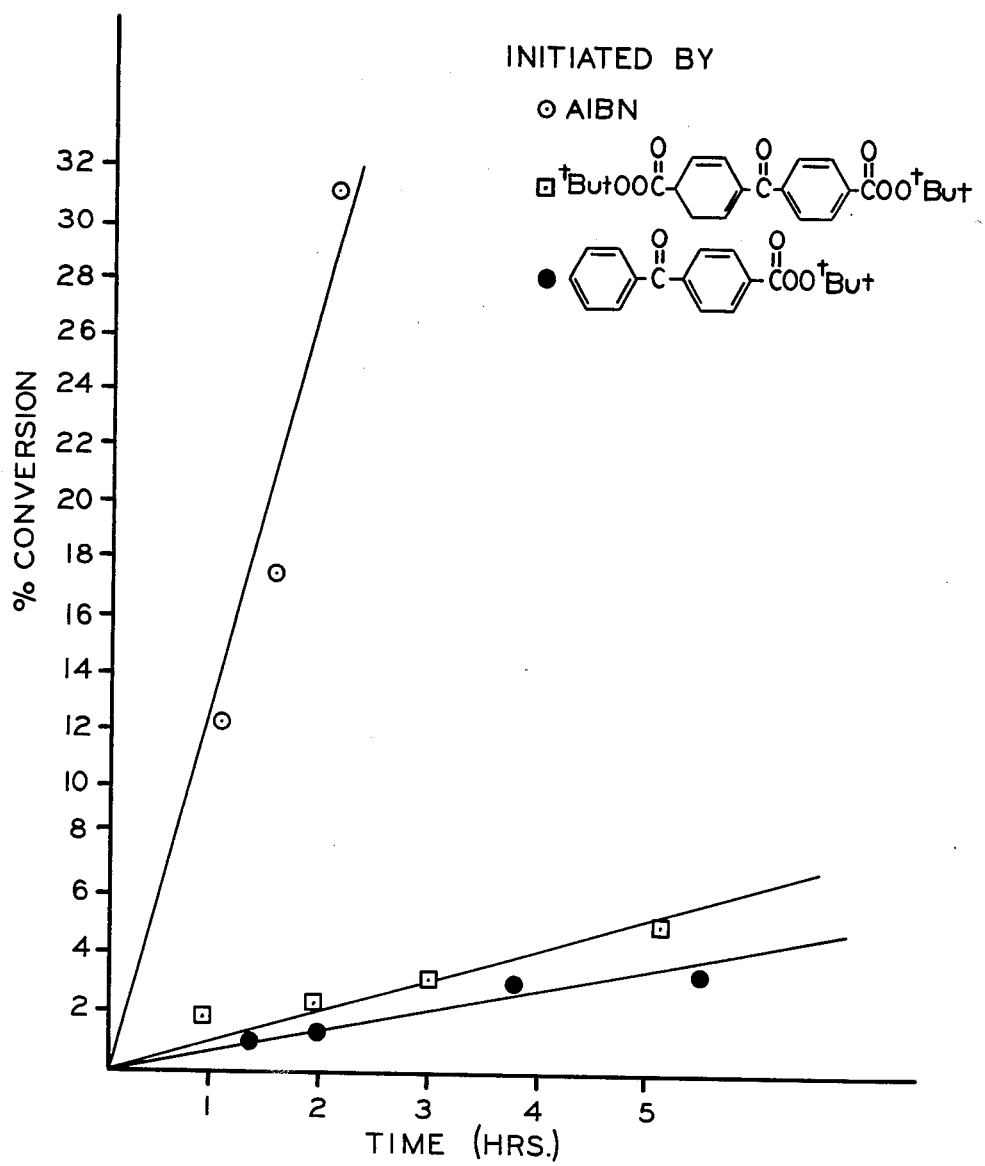
FIG. 20 is a graph showing thermal photopolymerization of methylmethacrylate (MMA) (bulk) at 70° C. in the dark.

FIG. 20 compares the thermal polymerization of MMA initiated by AIBN and both the monoperester and diperester. As anticipated from the known activation energies for thermolysis of tert-butyl perbenzoate and AIBN, the perbenzoates are much less effective initiators at 70° C.

Figure 21:
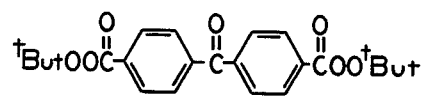
FIG. 21 is a graph showing dependence of the molecular weight of the polymer on the initiator concentration for photopolymerization of methylmethacrylate (MMA).
Figure 21:
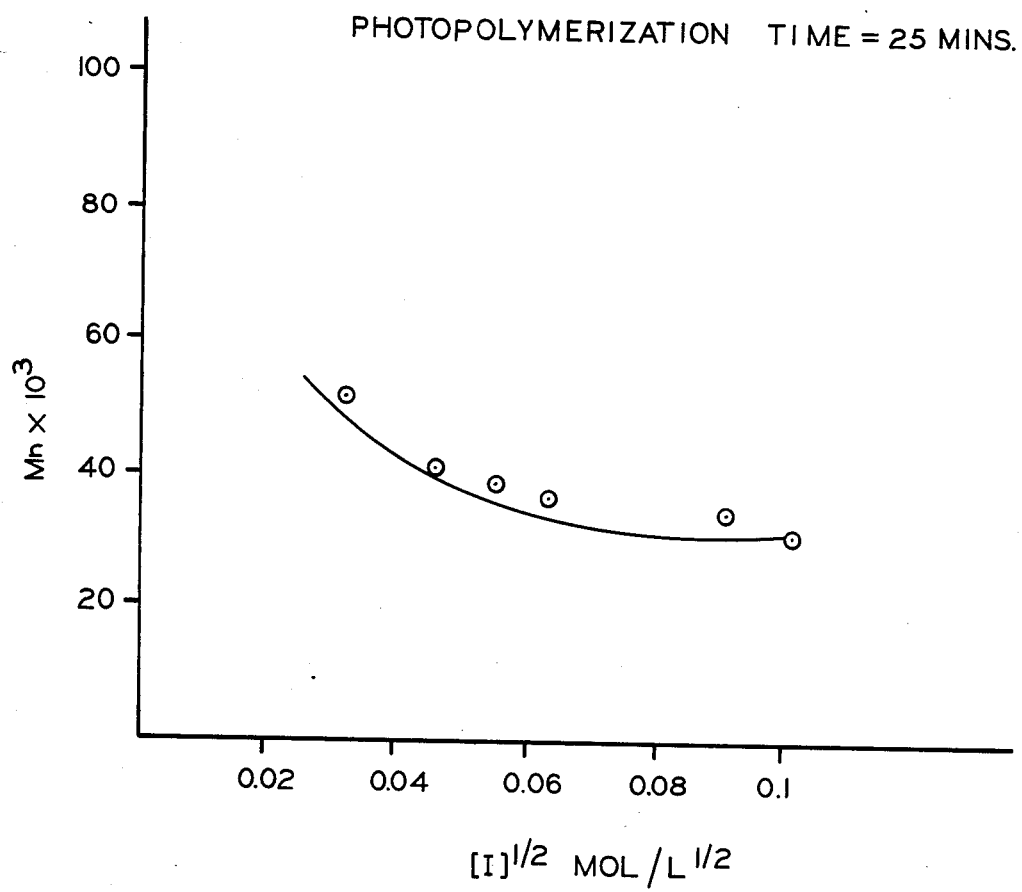

FIG. 21 shows that the molecular weight of the polymer produced is inversely proportional to the square root of the initiator concentration for the photoinitiated polymerization of both MMA and styrene. This is explained by chain transfer of the growing polymer chain on the O—O bond of the perester. This situation is more severe for the disperester than for the monoperester, as shown in FIG. 21.

Figure 22:
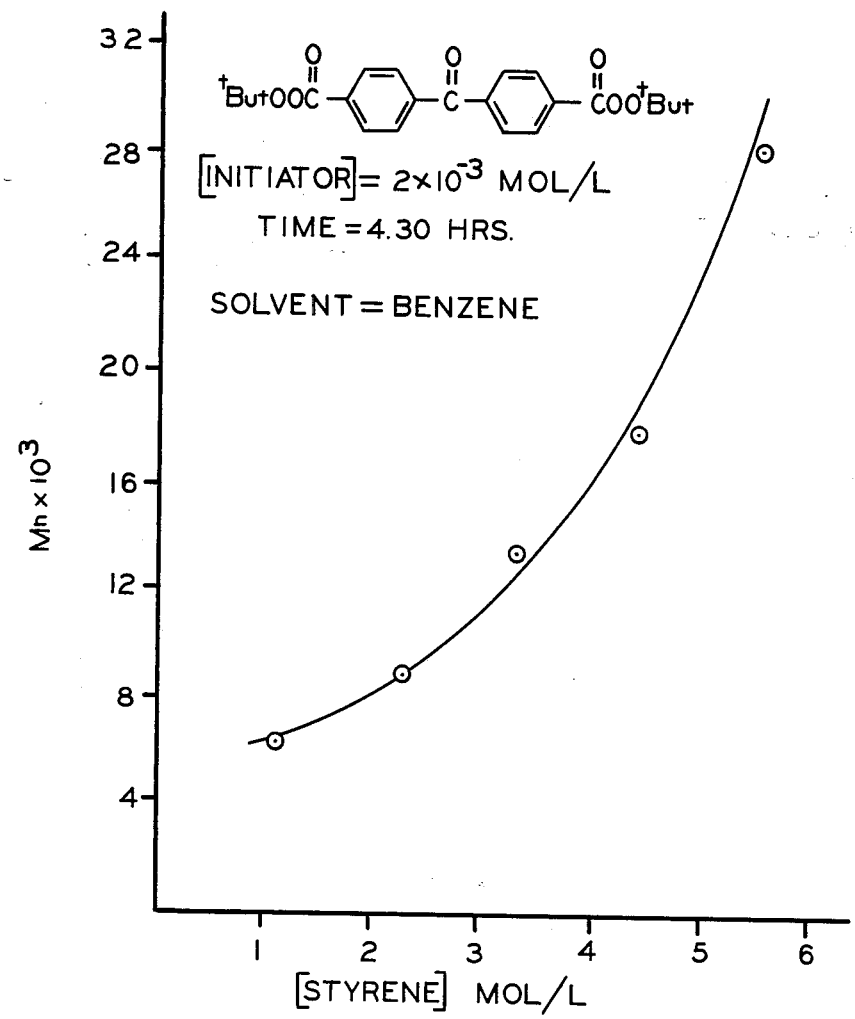
FIG. 22 is a graph showing dependence of the molecular weight of the polymer on the monomer concentration for photopolymerization of styrene.

FIG. 22 shows the relationship between the molecular weight of polystyrene produced and the concentration of the monomer. The molecular weight increases as the concentration of the monomer increases in the photochemically initiated reaction and this corresponds with the decreased rate of polymerization reported previously.

Table 9 shows that the molecular weight of polystyrene formed from the photoinitiated reaction increases with conversion. This derives from photochemical crosslinking of the formed polymer by processes which involve the benzophenone triplet state of the carbonyl-capped polymer chain. The molecular weight of the polystyrene produced from the diperester is lower than that produced from the monoperester, due to chain transfer on the remaining perester functionality.

TABLE 9

Photopolymerization of Styrene (Bulk) Initiated by

${}^tBuOOC-C_6H_4-C(O)-C_6H_4-COO^tBu$

[I] = 2.4 × 10$^{-3}$mol/l

| Time (min) | $M_n$ |
|---|---|
| 75 | $2.8 \times 10^4$ |
| 120 | $3.38 \times 10^4$ |
| 180 | $5.6 \times 10^4$ |

The above detailed description of the present invention is given for explanatory purposes. It will be apparent to those skilled in the art that numerous changes and modifications can be made in the preferred embodiments of the invention described above without departing from the scope of the invention. Accordingly, the whole of the foregoing description is to be construed in an illustrative and not in a limitative sense, the scope of the invention being defined solely by the appended claims.

I claim:

1. A perester compound of the formula

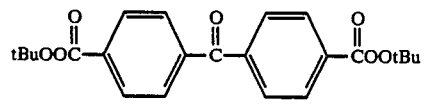
formed by reacting a compound of the formula:
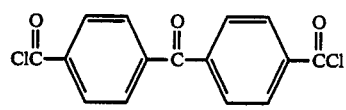
with tertiary butyl hydroperoxide.
2. A perester compound of the formula
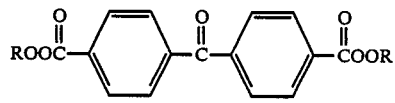
formed by reacting a compound of the formula:
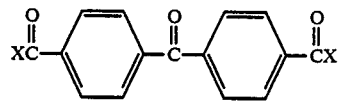
wherein X=Cl,OH with a hydroperoxide of the formula R—OOH wherein R is a tertiary butyl group.
* * * * *